US012734157B2

(12) United States Patent
Chen et al.

(10) Patent No.: US 12,734,157 B2
(45) Date of Patent: Sep. 15, 2026

(54) METHOD FOR PREVENTING AND/OR TREATING LIVER FIBROSIS BY USING 6-METHOXYBENZOXAZOLINONE AND COIX LACHRYMA-JOBI L. EXTRACT COMPRISING 6-METHOXYBENZOXAZOLINONE

(71) Applicant: Taichung District Agricultural Research and Extension Station, Ministry of Agriculture, Chang-Hwa County (TW)

(72) Inventors: Yu-Hsin Chen, Chang-Hwa County (TW); Cheng Huang, Chang-Hwa County (TW); Ching-Kuo Lee, Chang-Hwa County (TW); Yu-Lin Cai, Chang-Hwa County (TW)

(73) Assignee: TAICHUNG DISTRICT AGRICULTURAL RESEARCH AND EXTENSION STATION, MINISTRY OF AGRICULTURE, Chang-Hwa County (TW)

( * ) Notice: Subject to any disclaimer, the term of this patent is extended or adjusted under 35 U.S.C. 154(b) by 604 days.

(21) Appl. No.: 18/220,475

(22) Filed: Jul. 11, 2023

(65) Prior Publication Data

US 2025/0017907 A1 Jan. 16, 2025

(51) Int. Cl.

| | |
|---|---|
| ***A61K 31/423*** | (2006.01) |
| ***A61K 31/421*** | (2006.01) |
| ***A61P 1/16*** | (2006.01) |
| ***C07D 263/58*** | (2006.01) |

(52) U.S. Cl.
CPC .............. *A61K 31/421* (2013.01); *A61P 1/16* (2018.01)

(58) Field of Classification Search
CPC ............................ A61K 31/423; C07D 263/58
USPC .......................................... 514/375; 548/221
See application file for complete search history.

*Primary Examiner* — Douglas M Willis
(74) *Attorney, Agent, or Firm* — WPAT, PC

(57) ABSTRACT

The present disclosure provides a method for preventing and/or treating liver fibrosis by using 6-methoxybenzoxazolinone and a *Coix lachryma-jobi* L. extract including 6-methoxybenzoxazolinone of the following structural formula:

The 6-methoxybenzoxazolinone and the *Coix lachryma-jobi* L. extract including 6-methoxybenzoxazolinone of the present disclosure achieve the effect of preventing and/or treating liver fibrosis through various efficacy experiments.

11 Claims, 42 Drawing Sheets

Specification includes a Sequence Listing.

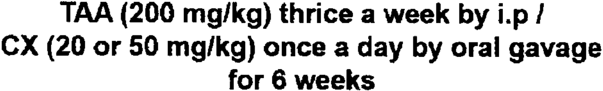
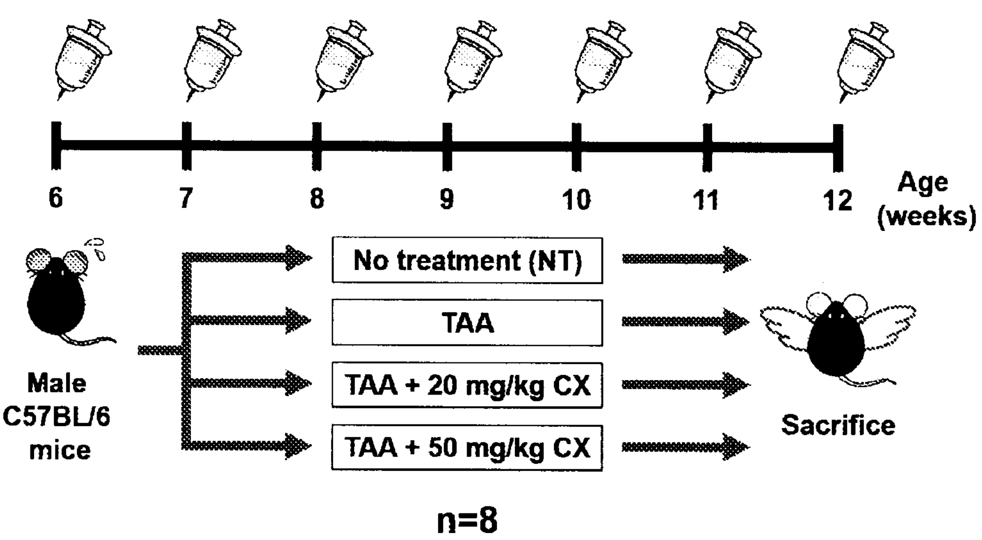
FIG. 6
FIG. 7A

Serum TC
mg/dL
200
150
100
50
0
b
a
c
ac
NT
TAA
CX20
CX50

IL-6

CX - - 10 20 50 100 (μM)
TGF-β1 - + + + + + (10 ng/mL)
p-SMAD2
p-SMAD3
SMAD2/3
SNAIL1/2
TWIST1/2
ZEB1
NOX4
α-Tubulin

METHOD FOR PREVENTING AND/OR TREATING LIVER FIBROSIS BY USING 6-METHOXYBENZOXAZOLINONE AND COIX LACHRYMA-JOBI L. EXTRACT COMPRISING 6-METHOXYBENZOXAZOLINONE

STATEMENT REGARDING SEQUENCE LISTING

The sequence listing associated with this application is provided in text format in lieu of a paper copy and is hereby incorporated by reference into the specification. The name of the XML file containing the sequence listing is sl. The XML file is 22101 bytes; was created on Jul. 11, 2023.

BACKGROUND OF THE INVENTION

1. Field of the Invention

The present invention relates to a method for preventing and/or treating liver fibrosis by using 6-methoxybenzoxazolinone (6-MBOA) and a *Coix lachryma-jobi* L. extract comprising 6-methoxybenzoxazolinone.

2. The Prior Art

The liver is an important organ in the human body, which is composed of parenchymal cells and non-parenchymal cells. Parenchymal cells, also known as hepatocytes, make up 60% of the cells in the overall liver and make up 80% of the volume of the liver. Non-parenchymal cells are composed of other biologically important cells, including sinusoidal endothelial cells, kupffer cells, hepatic stellate cells (HSCs), and hepatic natural killer cells, in which each type of cells disclosed above accounts for 3 to 20% of the number.

Liver fibrosis is excessive wound repair to injuries caused by viral infection, alcoholic liver disease (ALD), non-alcoholic fatty liver disease (NAFLD), autoimmune liver disease (AILD), and cholestatic liver injury. Accompanied by superfluous extracellular matrix (ECM) deposition, liver fibrosis not only changes liver structure but also undermines liver functions. Hepatic stellate cell (HSC) activation plays an essential role because activated HSCs are the main producers of ECM in a damaged liver.

At present, clinical liver fibrosis drug treatment has limited effect and has serious side effects, and many patients cannot continue to treat. More importantly, the drug only alleviates the symptoms, but fails to fundamentally solve the problem of neurodegeneration and death, so how to develop a new drug that can really treat and/or prevent liver fibrosis is an important issue that the present invention intends to solve here.

In order to solve the above-mentioned problems, those skilled in the art urgently need to develop a novel composition for preventing and/or treating liver fibrosis for the benefit of a large group of people in need thereof.

SUMMARY OF THE INVENTION

A primary objective of the present invention is to provide a method for preventing and/or treating liver fibrosis, comprising administering to a subject in need thereof a composition comprising an effective amount of 6-methoxybenzoxazolinone (6-MBOA).

According to an embodiment of the present invention, the 6-MBOA reduces inflammatory infiltration, liver structure deformation, collagen deposition, expression level of α-smooth muscle actin (α-SMA), liver hydroxyproline content, concentration of transforming growth factor-β1 (TGF-β1) in serum, liver weight, liver index, production of reactive oxygen species (ROS), and expression level of TGF-β1-induced fibronectin in the subject in need thereof.

According to an embodiment of the present invention, the 6-MBOA negatively regulates expression levels of phosphor-Mothers against decapentaplegic homolog 2 (p-SMAD2) and phosphor-Mothers against decapentaplegic homolog 3 (p-SMAD3) in the subject in need thereof.

According to an embodiment of the present invention, the 6-MBOA increases superoxide dismutase (SOD) activity, catalase (CAT) activity, glutathione (GSH) content, and decreases malondialdehyde (MDA) content.

According to an embodiment of the present invention, the 6-MBOA inhibits hepatic stellate cell (HSC) activation and epithelial-mesenchymal transition (EMT).

According to an embodiment of the present invention, the 6-MBOA decreases expression levels of Zinc finger protein SNAIL1/2, TWIST1/2, Zinc finger E-box-binding homeobox 1 (ZEB1), and NADPH oxidase 4 (NOX4).

Another objective of the present invention is to provide a method for preventing and/or treating liver fibrosis, comprising administering to a subject in need thereof a composition comprising an effective amount of *Coix lachryma-jobi* L. extract comprising 6-methoxybenzoxazolinone (6-MBOA).

According to an embodiment of the present invention, the *Coix lachryma-jobi* L. extract is obtained by extracting *Coix lachryma-jobi* L. with a solvent, and the solvent is water, alcohol, a mixture of alcohol and water, or a combination thereof.

According to an embodiment of the present invention, the *Coix lachryma-jobi* L. extract reduces serum levels of alanine aminotransferase (ALT), aspartate aminotransferase (AST), total bilirubin (TBIL), total glyceride (TG) and total cholesterol (TC) in the subject in need thereof.

According to an embodiment of the present invention, the *Coix lachryma-jobi* L. extract reduces levels of gene expression as well as protein including α-smooth muscle actin (α-SMA), collagen, type I, alpha 1 (COL1A1), fibronectin, and maintaining normal protein level of E-cadherin to that of the control, indicating epithelial-mesenchymal transition (EMT) is prevent. The gene expression (mRNA) of pro-inflammatory cytokine tumor necrosis factor-α (TNF-α) and interleukin-6 (IL-6) are reduced. In contrast anti-inflammatory cytokine interleukin (IL)-10 is increased, indicating the anti-inflammation properties of *Coix lacryma-jobi* L. extracts.

According to an embodiment of the present invention, the *Coix lachryma-jobi* L. is root, leaf or seed of the *Coix lachryma-jobi* L.

According to an embodiment of the present invention, the composition is a pharmaceutical composition, a food composition or a topical composition.

According to an embodiment of the present invention, the pharmaceutical composition is in a dosage form for oral administration.

According to an embodiment of the present invention, the pharmaceutical composition is in a dosage form for parenteral administration.

According to an embodiment of the present invention, the pharmaceutical composition further comprises a pharmaceutically acceptable excipient, carrier, adjuvant and/or food additive.

According to an embodiment of the present invention, the composition has a dosage form of powder, granule, solution, jelly or paste.

In summary, 6-methoxybenzoxazolinone (6-MBOA) and the *Coix lachryma-jobi* L. extract comprising 6-MBOA of the present invention achieve the effect on ameliorating liver fibrosis in vivo and in vitro, accompanied with downregulation of fibrotic and inflammatory factors. Furthermore, 6-MBOA improves oxidative stress in liver, as well as reduces the production of liver fibrotic biomarkers and promotes the loss of mesenchymal identity of HSC through the TGF-β/SMAD signaling pathway. Both 6-MBOA and the *Coix lachryma-jobi* L. extract comprising 6-MBOA possess therapeutic potential for liver fibrosis.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

In FIGS. 5C-5H, the letter "L", "R", "S" represent extracts of leaf, root and seed, respectively.

FIG. 6 is a schematic diagram of animal experiment design in 6-methoxybenzoxazolinone (6-MBOA) (CX) groups. For animal experiments, 6-week-old C57BL/6J mice were randomly divided into four groups including NT, TAA, CX20 (TAA+20 mg/kg CX), CX50 (TAA+50 mg/kg CX). (n=8 per group). Mice were given intraperitoneal injection of TAA thrice a week to induce liver fibrosis; they also received CX or the vehicle by oral gavage once per day. At the end of animal tests, mice were sacrificed at 12 weeks of age.

FIGS. 7A-7K show effects of CX on liver histopathology and physiological values in TAA-induced liver fibrotic C57BL/6J mice. (7A) Chemical structure of CX ($C_8H_7NO_3$, MW=165.15). (7B) Histological changes of liver observed with H&E, Sirius Red and IHC staining (original magnification×200, and the scale bar is 100 μm). (7C) Quantifications of Sirius Red staining of collagen. (7D-7F) Quantifications of IHC staining of α-SMA, phosphor-Mothers against decapentaplegic homolog 2 (phospho-SMAD2), and phosphor-Mothers against decapentaplegic homolog 3 (phospho-SMAD3). (7G) Changes in liver hydroxyproline contents. (7H) Expression of TGF-β1 in serum. (7I, 7J) Changes in liver and body weights. (7K) Liver index, the ratio of liver weight to body weight. Quantifications of Sirius Red and IHC staining is achieved by using image J software. Data were presented as mean±SD (n=8 per group). The bars are marked with different letters; the same letter indicates no significant difference between the two groups ($p>0.05$) while different letters indicate a significant difference between the two groups ($p<0.05$).

DETAILED DESCRIPTION OF THE PREFERRED EMBODIMENT

Figure 1:
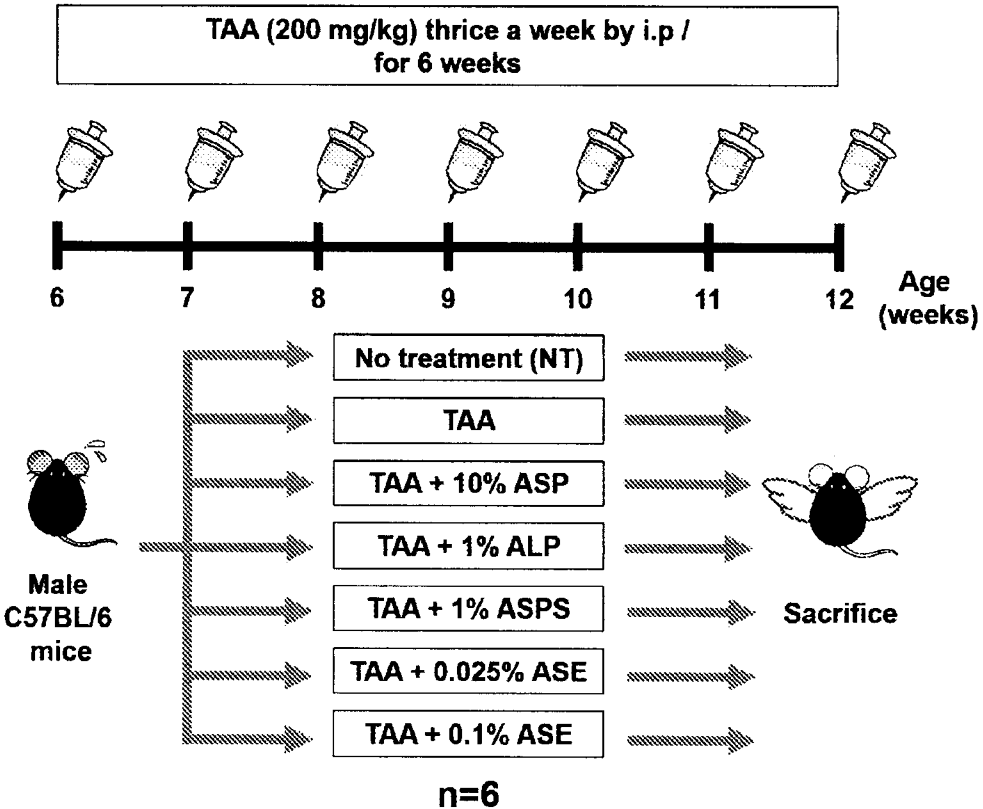
FIG. 1 is a schematic diagram of animal experiment design in adlay groups. In this experiment, C57BL/6J mice were intraperitoneally injected with thioacetamide (TAA) to induce liver fibrosis. At six weeks of age, the mice were randomly divided into seven groups fed with different diets (NT, TAA, 10% ASP, 1% ALP, 1% ASPS, 0.025% ASE and 0.1% ASE, n=6). After co-feeding for 6 weeks during which intraperitoneal injection of TAA was administered thrice a week, the mice were finally sacrificed at 12 weeks of age. NT represents no treatment, ASP represents adlay seed powder, ALP represents adlay leaf powder, ASPS represents adlay seed polysaccharide, and ASE represents adlay seed ethanolic extract.

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Definition

As used herein, the data provided represent experimental values that can vary within a range of ±20%, preferably within ±10%, and most preferably within ±5%.

Unless otherwise stated in the context, "a", "the" and similar terms used in the specification (especially in the following claims) should be understood as including singular and plural forms.

According to the present invention, *Coix lachryma-jobi* L. (e.g., *Coix lachryma-jobi* L. var. *ma-yuen* Stapf), also called Adlay, *coix* seeds, Chinese pearl barley, semen coicis, and yokuinin, is an annual or perennial herb of the Gramineae family. Adlay is a popular herbal medicine and food supplement in Asia, and is often taken to improve inflammatory diseases. It is about 1 to 1.8 meters high, usually blooms from July to September and bears fruits from September to October. Furthermore, the adlay seed consists of four parts from the outside to the inside, including the bran, hull, testa and endosperm (polished adlay), each with its own biological activities.

According to the present invention, 6-methoxybenzoxazolinone (6-MBOA) (CX) (formula: $C_8H_7NO_3$) is a compound from Gramineae plants, and has anti-diabetic and hormone-modulating activities.

According to the present invention, the pharmaceutical composition can be manufactured to a dosage form suitable for parenteral or oral administration, using techniques well known to those skilled in the art, including, but not limited to, injection (e.g., sterile aqueous solution or dispersion), sterile powder, tablet, troche, lozenge, pill, capsule, dispersible powder or granule, solution, suspension, emulsion, syrup, elixir, slurry, and the like.

The pharmaceutical composition according to the present invention may be administered by a parenteral route selected from the group consisting of: intraperitoneal injection, subcutaneous injection, intraepidermal injection, intradermal injection, intramuscular injection, intravenous injection, intralesional injection, sublingual administration, and transdermal administration.

The pharmaceutical composition according to the present invention can comprise a pharmaceutically acceptable carrier which is widely used in pharmaceutical manufacturing technology. For example, the pharmaceutically acceptable carrier can comprise one or more reagents selected from the group consisting of solvent, emulsifier, suspending agent, decomposer, binding agent, excipient, stabilizing agent, chelating agent, diluent, gelling agent, preservative, lubricant, absorption delaying agent, liposome, and the like. The selection and quantity of these reagents fall within the scope of the professional literacy and routine techniques of those skilled in the art.

According to the present invention, the pharmaceutically acceptable carrier comprises a solvent selected from the group consisting of water, normal saline, phosphate buffered saline (PBS), sugar solution, aqueous solution containing alcohol, and combinations thereof.

According to the present invention, the chemicals and reagents used in the following examples are described as follows. 6-methoxybenzoxazolinone (6-MBOA) (CX) (purity≥96.5%), thioacetamide (TAA) (purity≥99.0%), and 2',7'-Dichlorofluorescin diacetate (DCFDA, purity≥97.0%) were purchased from Sigma-Aldrich (Sigma-Aldrich, USA), Recombinant Human transforming growth factor beta 1 (TGF-β1) was from PeproTech (PeproTech, USA), TBARS and Catalase (CAT) Assay Kits were obtained from Cayman Chemical (Cayman Chemical, USA), Reduced Glutathione (GSH) and Superoxide Dismutase (SOD) Assay Kits were purchased from Abbkine (Abbkine Scientific, China) Hydroxyproline assay kit was brought from Elabscience (Elabscience Biotechnology, China). The mouse TGF-β1 ELISA kit was brought from Invitrogen (Thermo Fisher Scientific, USA). Antibodies against α-smooth muscle actin (α-SMA) (GTX100458), collagen, type I, alpha 1 (COL1A1) (GTX112731), fibronectin (GTX112794), E-cadherin (GTX629691), NADPH oxidase 4 (NOX4) (GTX121929), TWIST1/2 (GTX127310), Zinc finger E-box-binding homeobox 1 (ZEB1) (GTX105278), β-actin (GTX109639), α-Tubulin (GTX628802), phosphor-Mothers against decapentaplegic homolog 2 (phospho-SMAD2) (GTX133614), phosphor-Mothers against decapentaplegic homolog 3 (phospho-SMAD3) (GTX129841), phospho-extracellular signal-regulated kinase 1/2 (ERK1/2) (GTX635617), phospho-phosphoinositide 3-kinase (PI3K) (GTX132597), SMAD2/3 (GTX111123), and horseradish peroxidase (HRP) bought from GeneTex (GeneTex, USA). In addition, Zinc finger protein SNAIL1/2 (ab180714) was bought from Abcam (Abcam, UK).

According to the present invention, animals used in the following examples are described as follows. Male C57BL/6J mice (5-week-old) were from the National Laboratory Animal Center (Taipei, Taiwan), and housed in a temperature-controlled room on a 12 h light-dark cycle with free access to food and drinking water at the Animal Center of the National Yang Ming Chiao Tung University (Taipei, Taiwan). All experiments were approved by Institutional Animal Care and Use Committee of National Yang Ming Chiao Tung University.

For tests of adlay extracts, mice were randomly divided into the following seven groups (n=6, per group): (1) No treatment group (NT, normal diet), (2) Thioacetamide group (TAA, 200 mg/kg, normal diet), (3) 10% adlay seed powder (ASP) group, (4) 1% adlay leaf powder (ALP) group, (5) 1% adlay seed polysaccharide (ASPS) group, (6) 0.025% adlay seed ethanolic extract (ASE) group and (7) 0.1% ASE group. NT group received pure saline, and other groups intraperitoneally injected with TAA dissolved into saline thrice a week.

For tests of CX, mice were randomly divided into the following four groups (n=8, per group): (1) NT group, (2) TAA group (200 mg/kg), (3) CX group (CX20, 20 mg/kg), and (4) CX group (CX50, 50 mg/kg). NT group received pure saline, and other groups intraperitoneally injected with TAA dissolved into saline thrice a week. Moreover, NT group and TAA group also received 5% propylene glycol, while CX groups received CX dissolved into 5% propylene glycol (prepared in 0.9% saline) by oral gavage once per day.

At the end of the experiment, the mice were sacrificed. Serum was obtained from the whole blood of mice after centrifuging and stored at −80° C., and the liver tissues were collected and used for the tissue histological staining.

According to the present invention, the procedure of statistical analysis is as follows. Statistical analysis was performed with one-way ANOVA followed by Tukey's multiple comparisons test in GraphPad Prism 7. And the data of cell viability were performed with two-way ANOVA followed by Dunnett's multiple comparisons test. All the data were presented as mean±standard deviation (SD). Differences of P-value<0.05 were considered statistically significant.

Example 1

Preparation of *Coix lachryma-jobi* L. Extracts

For cell experiments, different parts of the adlay were used, including leaves (L), roots (R), and seeds (S). After drying and grinding, the adlay was extracted with water, alcohol, a mixture of alcohol and water, or a combination thereof (preferably 70% ethanol), concentrated and dried under reduced pressure. On the other hand, adlay seed powder (ASP, normal diet with 10% ASP), adlay leaf powder (ALP, normal diet with 1% ALP), adlay seed polysaccharide (ASPS, normal diet with 1% ASPS), and adlay seed ethanolic extract (ASE, normal diet with 0.025% and 0.1% ASE) were used for the animal tests. All the adlay extracts were kindly provided by Dr. Yu-Hsin Chen (Agricultural Improvement Center, Taiwan).

The procedure of the schematic diagram of animal experiment design in adlay groups is described as follows. To examine the effects of adlay on liver fibrosis, this example established a TAA-induced liver fibrotic C57BL/6J mouse model. FIG. 1 is a schematic diagram of animal experiment design in adlay groups. In this experiment, C57BL/6J mice were intraperitoneally injected with thioacetamide (TAA) to induce liver fibrosis. At six weeks of age, the mice were randomly divided into seven groups fed with different diets (NT, TAA, 10% ASP, 1% ALP, 1% ASPS, 0.025% ASE and 0.1% ASE, n=6). After co-feeding for 6 weeks during which intraperitoneal injection of TAA was administered thrice a week, the mice were finally sacrificed at 12 weeks of age. NT represents no treatment, ASP represents adlay seed powder, ALP represents adlay leaf powder, ASPS represents adlay seed polysaccharide, and ASE represents adlay seed ethanolic extract. Six-week-old mice were randomly divided into seven groups, including the NT, TAA, 10% ASP, 1% ALP, 1% ASPS, 0.025% ASE and 0.1% ASE groups (see FIG. 1). The NT and TAA groups received normal diet, while the adlay groups had adlay extracts added to the normal diet. Furthermore, TAA or saline was administered to mice by intraperitoneal injection thrice a week for six weeks. After six weeks, the mice were sacrificed, and their liver tissues and serum were collected for subsequent analyses.

Example 2

Effects of *Coix lachryma-jobi* L. Extract on Liver Histopathology and Physiological Values in TAA-Induced Liver Fibrotic Mice After six weeks of exposure, TAA-induced pathological changes in hematoxylin and eosin (H&E)- and immunohistochemistry (IHC)-stained liver tissue sections were observed.

The procedure of liver histopathological observation is as follows. After fixation in 10% neutral buffered formalin solution, the liver tissues were embedded with paraffin and then sliced into 4 μm-thickness sections. Pathological sections were examined to assess the change of tissue architecture with the H&E staining kit (CIS-Biotechnology, Taiwan), the condition of collagen deposition with the Sirius Red staining kit (CIS-Biotechnology, Taiwan), and the expression of specific proteins in tissue with the immunohistochemistry kit (Agilent, USA), as well as phospho-SMAD2 (1:100; GeneTex, USA), phospho-SMAD3 (1:100; GeneTex, USA), and α-SMA (1:100; GeneTex, USA) antibodies. All staining was observed with a light microscope (BEL Photonics, Italia).

The procedure of hydroxyproline assay is as follows. The hydroxyproline, as an indirect index of the collagen content in the liver, was determined by a hydroxyproline assay kit and the testing procedures followed the manufacturer's protocol. Briefly, liver tissue samples were hydrolyzed with HCl at 95° C. for 6 h, then the pH value was adjusted to 7, and the carbon powder was used to adsorb the impurities, centrifuged, and the supernatant was collected for analysis. The hydroxyproline content was measured at a wavelength of 558 nm on an ELISA reader (TECAN, Switzerland).

FIGS. 2A-2F show effects of the *Coix lachryma-jobi* L. extract on liver histopathology and physiological values in TAA-induced liver fibrotic C57BL/6J mice. (2A) Histopathological changes of liver observed with hematoxylin and eosin (H&E) and immunohistochemistry (IHC) staining (original magnification×200, and the scale bar is 100 μm). (2B) Quantifications of IHC staining of α-smooth muscle actin (α-SMA) performed using image J software. (2C) Changes in liver hydroxyproline contents. (2D, 2E) Changes in liver weights and body weights. (2F) Liver index, ratio of change of liver weight divided by body weight. Data were presented as mean±standard deviation (SD) (n=6 per group). The bars are marked with different letters; the same letter indicates no significant difference between the two groups ($p>0.05$) while different letters indicate a significant difference between the two groups ($p<0.05$).

Figure 2A:
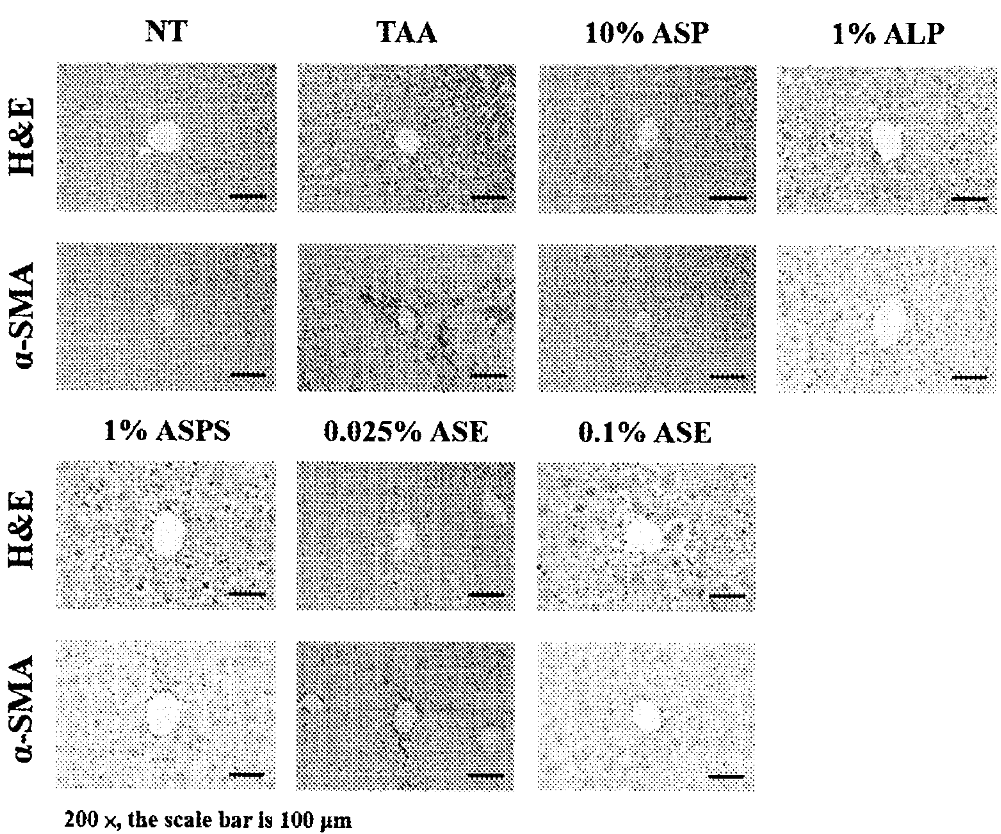
FIGS. 2A-2F show effects of the *Coix lachryma-jobi* L. extract on liver histopathology and physiological values in TAA-induced liver fibrotic C57BL/6J mice. (2A) Histopathological changes of liver observed with hematoxylin and eosin (H&E) and immunohistochemistry (IHC) staining (original magnification×200, and the scale bar is 100 μm). (2B) Quantifications of IHC staining of α-smooth muscle actin (α-SMA) performed using image J software. (2C) Changes in liver hydroxyproline contents. (2D, 2E) Changes in liver weights and body weights. (2F) Liver index, ratio of change of liver weight divided by body weight. Data were presented as mean±standard deviation (SD) (n=6 per group). The bars are marked with different letters; the same letter indicates no significant difference between the two groups ($p>0.05$) while different letters indicate a significant difference between the two groups ($p<0.05$).
Figure 2B:
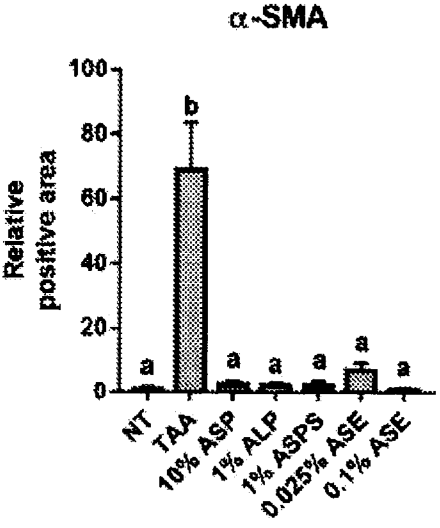
Figure 2C:
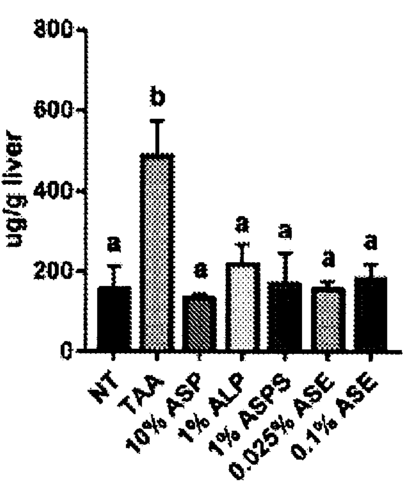
Figure 2D:
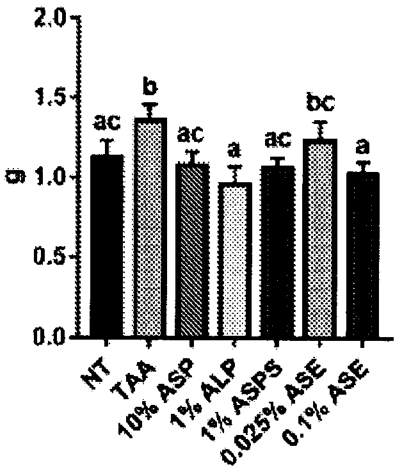
Figure 2E:
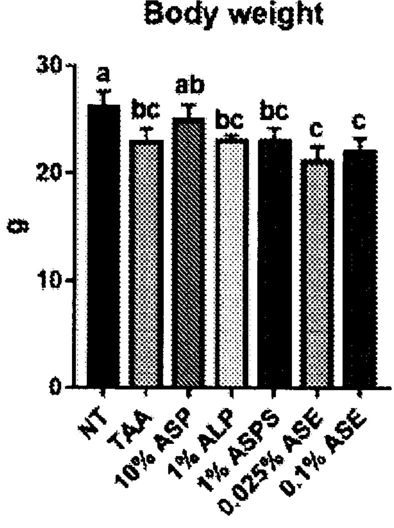
Figure 2F:
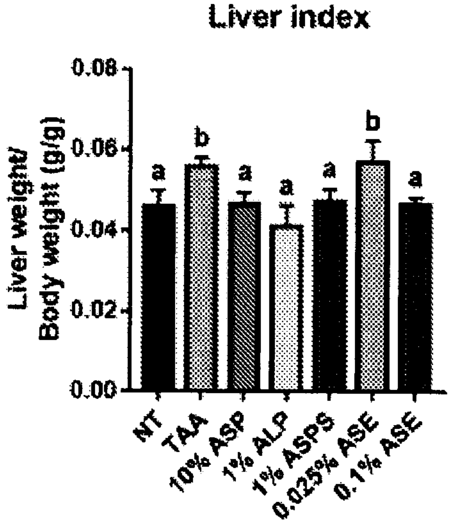

Compared with the NT group, the TAA group had induced inflammatory infiltration, deformation of liver architecture, and excessive expression of α-SMA (FIGS. 2A and 2B), while the adlay groups had significantly reduced inflammatory infiltration, improved liver deformation, and declined α-SMA expression. To detect the change in collagen content in the liver, the hydroxyproline (collagen component) assay was performed. Results showed that the TAA group had more hydroxyproline contents than the NT group, indicating an increase in collagen (FIG. 2C). On the other hand, all adlay groups had significantly decreased hydroxyproline content, suggesting that adlay reduced TAA-induced collagen deposition in the liver. Weight loss and liver tissue enlargement were observed in the TAA group compared with the NT group (FIGS. 2D and 2E). Among the adlay groups, the 10% ASP, 1% ALP, 1% ASPS, and 0.1% ASE groups showed significantly decreased liver enlargement caused by TAA, but there was no apparent difference in body weight. To avoid individual differences, the changes in liver weight and body weight were corrected by the liver index (FIG. 2F). Compared with the TAA group, only the 0.025% ASE group did not show an apparent change, while others had significantly decreased liver index.

Example 3

Effects of *Coix lachryma-jobi* L. Extract on Liver Biochemical Characterization in TAA-Induced Liver Fibrotic Mice The procedure of biochemical analysis is as follows. The levels of serum alanine aminotransferase (ALT), aspartate aminotransferase (AST), total bilirubin (TBIL), alkaline phosphatase (ALP), total cholesterol (TC), total glyceride (TG), and glucose were measured with the chemistry analyzer. Briefly, after centrifuging the whole blood from mice, collected the serum, dropped the serum at the tested chips for analysis with an Automated Clinical Chemistry Analyzer (Fuji, Japan).

FIGS. 3A-3F show effects of the *Coix lachryma-jobi* L. extract on liver function and nutrient metabolism in TAA-induced liver fibrotic C57BL/6J mice. (3A-3C) Serum levels of liver functional indexes alanine aminotransferase (ALT), aspartate aminotransferase (AST), and total bilirubin (TBIL). (3D-3F) Serum levels of total glyceride (TG), total cholesterol (TC), and glucose, for observing the nutrient metabolism. Data were presented as mean±SD (n=6 per group). The bars are marked with different letters; the same letter indicates no significant difference between the two groups ($p>0.05$) while different letters indicate a significant difference between the two groups ($p<0.05$).

Figure 3A:
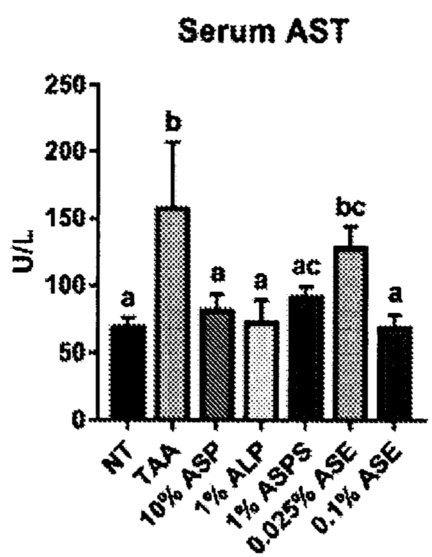
FIGS. 3A-3F show effects of the *Coix lachryma-jobi* L. extract on liver function and nutrient metabolism in TAA-induced liver fibrotic C57BL/6J mice. (3A-3C) Serum levels of liver functional indexes alanine aminotransferase (ALT), aspartate aminotransferase (AST), and total bilirubin (TBIL). (3D-3F) Serum levels of total glyceride (TG), total cholesterol (TC), and glucose, for observing the nutrient metabolism. Data were presented as mean±SD (n=6 per group). The bars are marked with different letters; the same letter indicates no significant difference between the two groups ($p>0.05$) while different letters indicate a significant difference between the two groups ($p<0.05$).
Figure 3B:
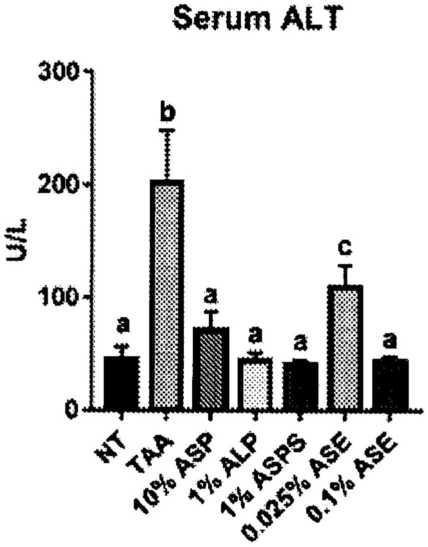
Figure 3C:
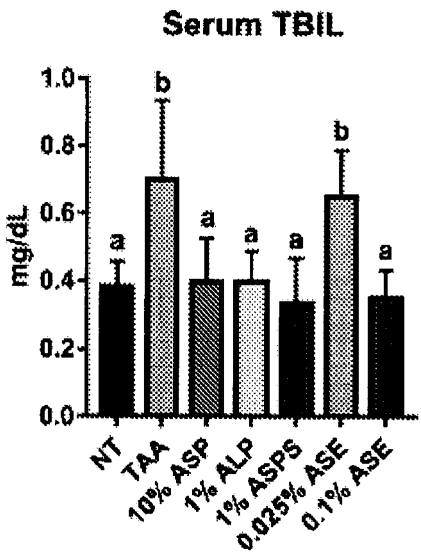
Figure 3D:
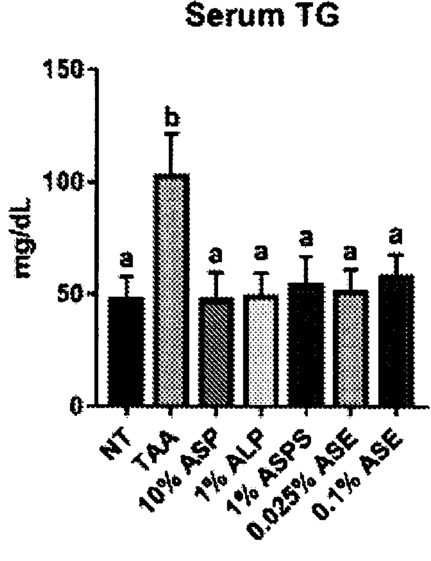
Figure 3E:
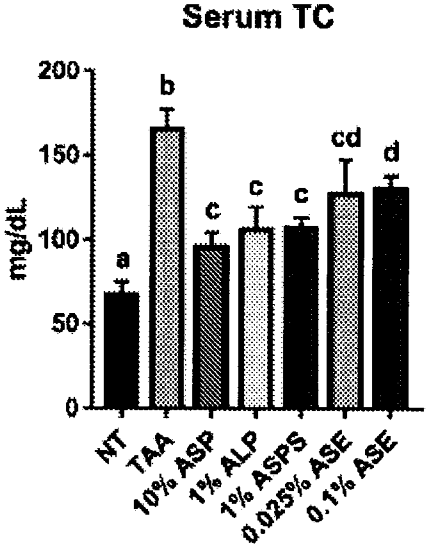
Figure 3F:
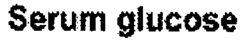
Figure 3F:
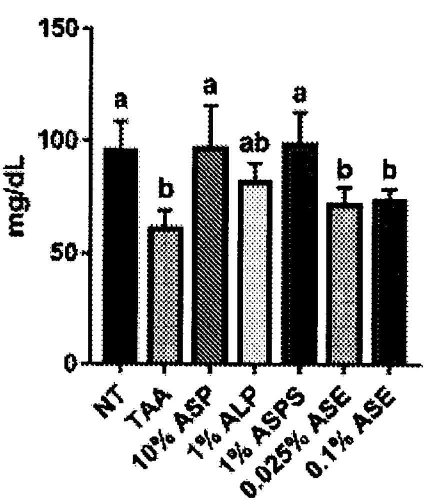

Serum AST, ALT, and TBIL are indices of liver functions, whereas serum TG, TC, and glucose are related to nutrient metabolism in the liver. Compared with the NT group, only the TAA group showed increased AST, ALT, and TBIL levels (FIGS. 3A-3C). In contrast, the adlay groups had downregulated TAA-caused upregulation of liver functional indexes, especially in groups of 10% ASP, 1% ALP, 1% ASPS, and 0.1% ASE. On the other hand, compared with the NT group, the TAA group showed significantly increased TG and TC levels and decreased glucose values (FIGS. 3D-3F). Treatment with the *Coix lachryma-jobi* L. extract significantly improved TAA-caused TG and TC levels in all adlay groups, and significantly increased glucose values in the 10% ASP and 1% ASPS groups.

Example 4

Effects of *Coix lachryma-jobi* L. Extract on Liver mRNA Levels of Fibrotic and Inflammatory Genes in TAA-Induced Liver Fibrotic Mice The procedure of real-time PCR analysis is as follows. Total RNA was extracted with the Trizol reagent (Ambion, USA) and then reverse-transcribed into cDNA with RevertAid First Strand cDNA Synthesis kit (Thermo Scientific, USA). The PCR amplification was accomplished with SYBR Green PCR Master Mix (Applied Biosystems, USA), and the mRNA expression of the gene was normalized to GAPDH. All primers were obtained from Genomics (Genomics, Taiwan). The primer sequences used in this example are listed in Table 1. Rat primer sequences are used for real-time PCR of HSC-T6 cells, and mouse primer sequences are used for real-time PCR of C57BL/6J mice.

TABLE 1

| Primer name | Species | Forward sequences | Reverse sequences |
|---|---|---|---|
| α-SMA | Rat | GCTCTGGTGTGTG ACAATGG (SEQ ID NO: 1) | CTTTTCCATGTC GTCCCAGT (SEQ ID NO: 2) |
| COL1A1 | Rat | TGTTCAGCTTTGTG GACCTC (SEQ ID NO: 3) | GCCATTGTGGC AGATACAGA (SEQ ID NO: 4) |
| GAPDH | Rat | GGCACAGTCAAGG CTGAGAATG (SEQ ID NO: 5) | ATGGTGGTGAA GACGCCAGTA (SEQ ID NO: 6) |
| IL-6 | Rat | ATTGTATGAACAG CGATGATGCAC (SEQ ID NO: 7) | CCAGGTAGAAA CGGAACTCCAG A (SEQ ID NO: 8) |
| IL-10 | Rat | GCGACGCTGTCAT CGATTTC (SEQ ID NO: 9) | GTAGATGCCGG GTGGTTCAA (SEQ ID NO: 10) |
| TNF-α | Rat | TCAGTTCCATGGC CCAGAC (SEQ ID NO: 11) | GTTGTCTTTGAG ATCCATGCCAT T (SEQ ID NO: 12) |
| α-SMA | Mice | GTCCCAGACATCA GGGAGTAA (SEQ ID NO: 13) | TCGGATACTTC AGCGTCAGGA (SEQ ID NO: 14) |
| COL1A1 | Mice | TGGATTCCCGTTCG AGTACG (SEQ ID NO: 15) | ATTAGGCGCAG GAAGGTCAG (SEQ ID NO: 16) |
| GAPDH | Mice | AACTTTGGCATTGT GGAAGG (SEQ ID NO: 17) | GGATGCAGGGA TGATGTTCT (SEQ ID NO: 18) |
| IL-6 | Mice | CCAGTTGCCTTCTT GGGACT (SEQ ID NO: 19) | GGTCTGTTGGG AGTGGTATCC (SEQ ID NO: 20) |
| IL-10 | Mice | GCTCTTACTGACTG GCATGAG (SEQ ID NO: 21) | CGCAGCTCTAG GAGCATGTG (SEQ ID NO: 22) |
| TNF-α | Mice | TGGGAGTAGACAA GGTACAACCC (SEQ ID NO: 23) | CATCTTCTCAA AATTCGAGTGA CAA (SEQ ID NO: 24) |

To confirm gene-level changes in liver fibrotic mice, the mRNA levels of fibrotic genes were observed using real-time PCR. FIGS. 4A-4E show effects of the *Coix lachryma-jobi* L. extract on fibrotic and inflammatory gene levels in TAA-induced liver fibrotic C57BL/6J mice. (4A, 4B) mRNA levels of fibrotic markers α-SMA and collagen, type I, alpha 1 (COL1A1). (4C-4E) mRNA levels of inflammatory cytokines tumor necrosis factor-α (TNF-α), interleukin-6 (IL-6), and IL-10. Data were presented as mean±SD (n=6 per group). The bars are marked with different letters; the same letter indicates no significant difference between the two groups ($p>0.05$) while different letters indicate a significant difference between the two groups ($p<0.05$).

Figure 4A:
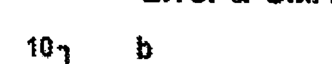
FIGS. 4A-4E show effects of the *Coix lachryma-jobi* L. extract on fibrotic and inflammatory gene levels in TAA-induced liver fibrotic C57BL/6J mice. (4A, 4B) mRNA levels of fibrotic markers α-SMA and collagen, type I, alpha 1 (COL1A1). (4C-4E) mRNA levels of inflammatory cytokines tumor necrosis factor-α (TNF-α), interleukin-6 (IL-6), and IL-10. Data were presented as mean±SD (n=6 per group). The bars are marked with different letters; the same letter indicates no significant difference between the two groups ($p>0.05$) while different letters indicate a significant difference between the two groups ($p<0.05$).
Figure 4A:
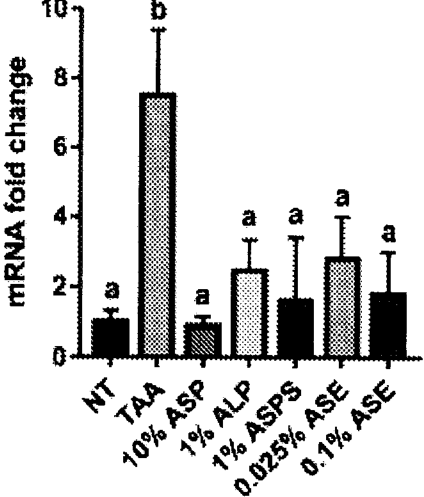
Figure 4B:
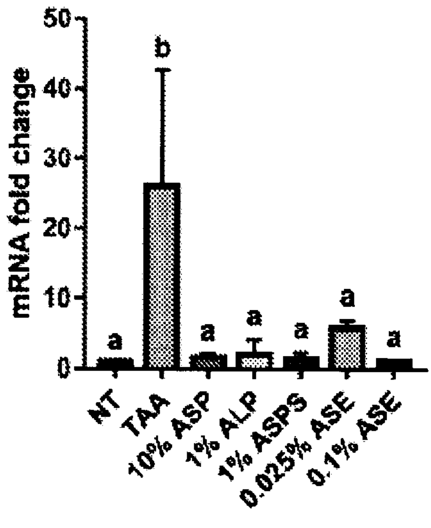
Figure 4C:
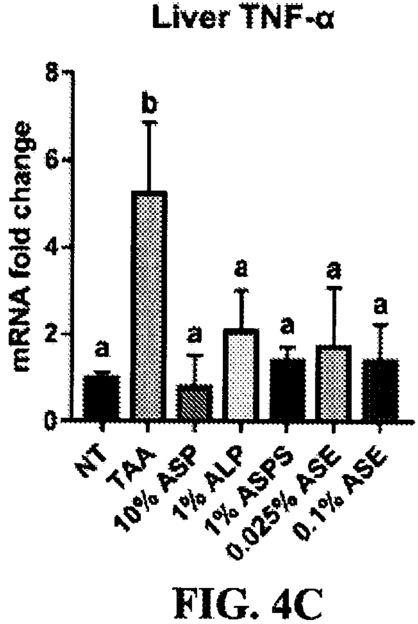
Figure 4D:
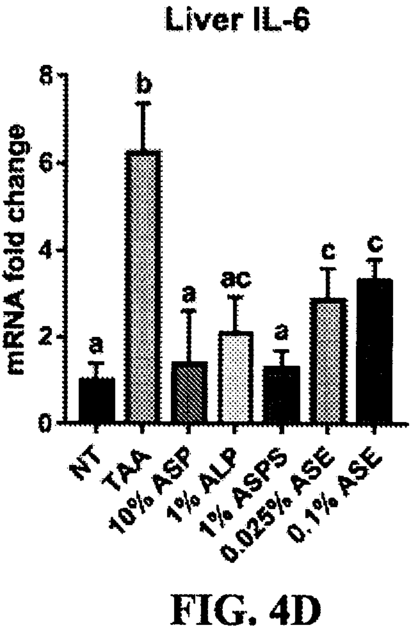
Figure 4E:
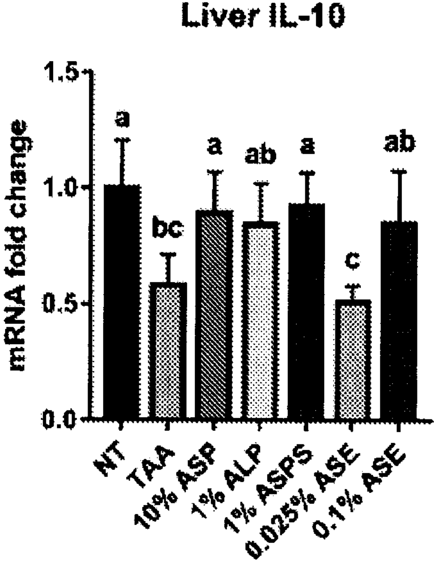

Compared with the NT group, the TAA group showed significantly increased fibrotic markers α-SMA and type 1 collagen (COL1A1) levels (FIGS. 4A and 4B). On the contrary, all adlay groups had significantly decreased α-SMA and COL1A1 levels, indicating that adlay reduced the expression of fibrotic markers. Inflammation is closely associated with fibrogenesis; hence, mRNA levels of inflammatory genes were also detected. Tumor necrosis factor-α (TNF-α) and IL-6 are pro-inflammatory cytokines, while IL-10 is an anti-inflammatory cytokine. Real-time PCR results showed upregulation of TNF-α and IL-6 as well as downregulation of IL-10 in the TAA group compared with the NT group (FIGS. 4C-4E). All adlay groups had reduced TAA-induced increase in TNF-α and IL-6 mRNA levels as well as significantly upregulated IL-10 mRNA levels, though the 1% ALP, 0.025% ASE, and 0.1% ASE groups did not differ significantly from the TAA group.

Example 5

Effects of *Coix lachryma-jobi* L. Extract on Cell Viability, Fibrotic Protein Expression, and Inflammatory Gene Levels in HSC-T6 Cells The procedure of cell cultures is as follows. HSC-T6 cell is an immortalized cell line isolated from transformed SV40 large T-antigen transformed primary stellate cells of male Sprague-Dawley rats. HSC-T6 cells were maintained in Dulbecco's Modified Eagle Medium (DMEM, Sigma-Aldrich, USA) containing 8% fetal bovine serum (FBS, HyClone, USA), 100 U/mL of penicillin, and 100 μg/mL of streptomycin (Gibco, USA).

For hepatic stellate cell (HSC) activation, cells were cultured for 24 h and then replaced with serum-free medium for 24 h, after that, treated with transforming growth factor beta 1 (TGF-β1) (10 ng/mL) in the presence or absence of CX (10-100 μM) or adlay leaf, root, and seed extracts (25 and 50 μg/mL) for 24 h, or 30 min for intracellular signal pathways.

The procedure of cell viability assay is as follows. HSC-T6 cells were seed at $1.5\times10^4$ in 96-well plates and were incubated with CX (0-800 μM) or adlay extracts (0-800 μg/mL) for 24 h. Followed by the determination of cell viability with MTT [3-(4,5-Dimethyl-2-thiazolyl)-2,5-diphenyl-2H-tetrazolium bromide] (Sigma-Aldrich, USA). Briefly, MTT was added to each well at a final concentration of 0.5 μg/mL and was incubated at 37° C. for 1 h. Next, removed the MTT and added the DMSO to dissolve MTT-formazan crystals formed by metabolically viable cells. Finally, the absorbance of each well was detected by a spectrophotometer at the wavelength of 570 nm.

The procedure of Western blot analysis is as follows. Cells were lysed in RIPA buffer with protease inhibitor and then centrifuged at 4° C., 12000 rpm for 10 min. Collected the supernatant and quantified the total protein concentration to 50 μg. After heating at 95° C. for 10 min, the protein samples were separated by SDS-PAGE gel, transferred to PVDF membrane, followed by blocking with 6% milk, incubated with primary antibodies at 4° C., overnight and secondary antibodies at room temperature for 1 h. Blot images were visualized on Amersham Imager 680 (Cytiva, USA) with ECL agent (GeneDireX, USA).

HSC activation is considered a primary event in liver fibrosis. This example used HSC-T6 cells as a cell model and added TGF-β1 to be an inducer of HSC activation.

FIGS. 5A-5H show effects of the *Coix lachryma-jobi* L. extract on cell viability, fibrotic protein expression, and inflammatory gene levels in HSC-T6 cells. (5A) Schematic representation of drug treatment in HSC-T6 cells. (5B) Cell viability of HSC-T6 cells treated with adlay leaf, root, and seed extracts. (5C-5E) Western blot results of α-SMA and COL1A1 in HSC-T6 cells treated with TGF-β1 and adlay extracts, and quantification of results using image J software. (5F-5H) mRNA levels of inflammatory factors in HSC-T6 treated with TGF-β1 and adlay extracts. Data were presented as mean±SD (n=3 per group). The bars of cell viability are marked with *, 0 of concentration vs. other concentrations, marked with  ($p<0.01$); * ($p<0.001$). The bars of western blot and real-time PCR are marked with different letters; the same letter indicates no significant difference between the two groups ($p>0.05$) while different letters indicate a significant difference between the two groups ($p<0.05$). In FIG. 5C~5H, the letter "L", "R", "S" represent extracts of leaf, root and seed, respectively.

Figure 5A:
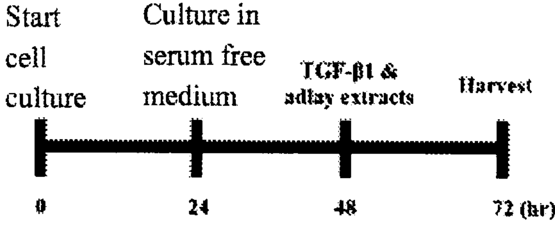
FIGS. 5A-5H show effects of the *Coix lachryma-jobi* L. (adlay) extract on cell viability, fibrotic protein expression, and inflammatory gene levels in HSC-T6 cells. (5A) Schematic representation of drug treatment in HSC-T6 cells. (5B) Cell viability of HSC-T6 cells treated with adlay leaf, root, and seed extracts. (5C-5E) Western blot results of α-SMA and COL1A1 in HSC-T6 cells treated with TGF-β1 and adlay extracts, and quantification of results using image J software. (5F-5H) mRNA levels of inflammatory factors in HSC-T6 treated with TGF-β1 and adlay extracts. Data were presented as mean±SD (n=3 per group). The bars of cell viability are marked with *, 0 of concentration vs. other concentrations, marked with  ($p<0.01$); * ($p<0.001$). The bars of western blot and real-time PCR are marked with different letters; the same letter indicates no significant difference between the two groups ($p>0.05$) while different letters indicate a significant difference between the two groups ($p<0.05$).
Figure 5B:
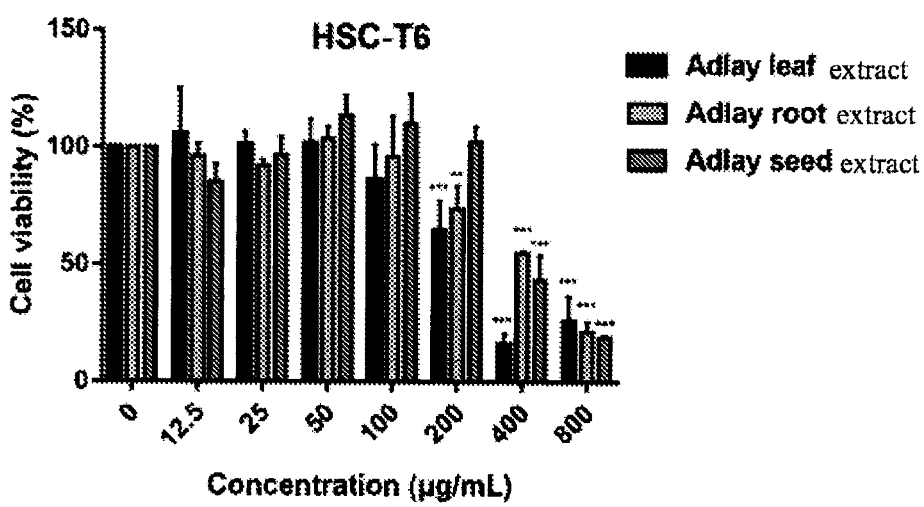
Figure 5C:
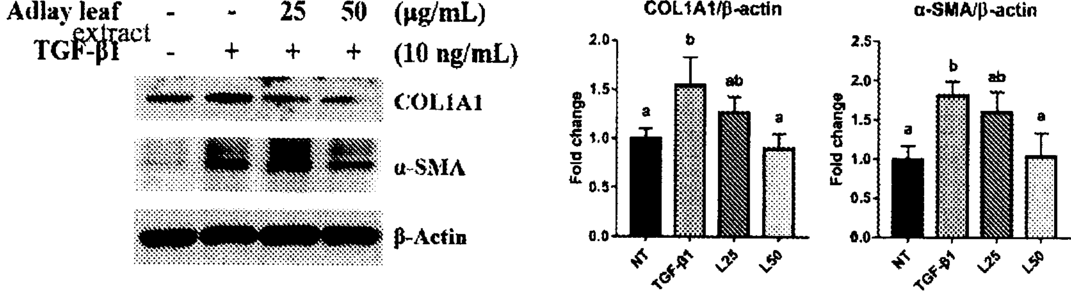
Figure 5D:
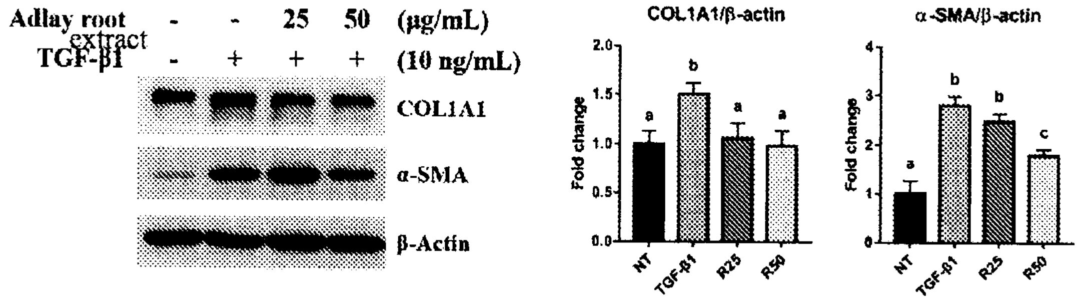
Figure 5E:
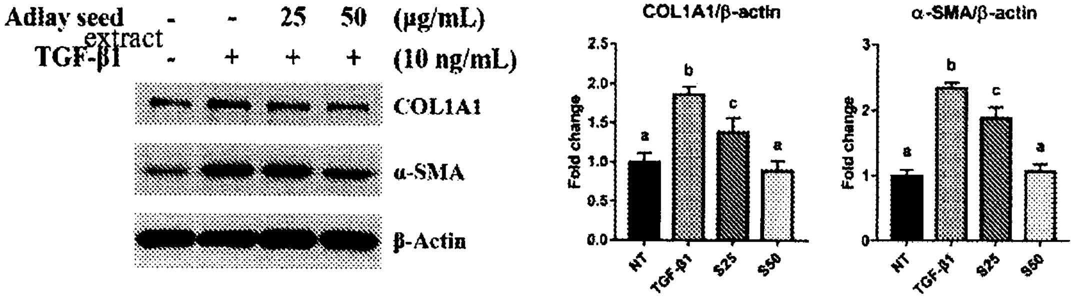
Figure 5F:
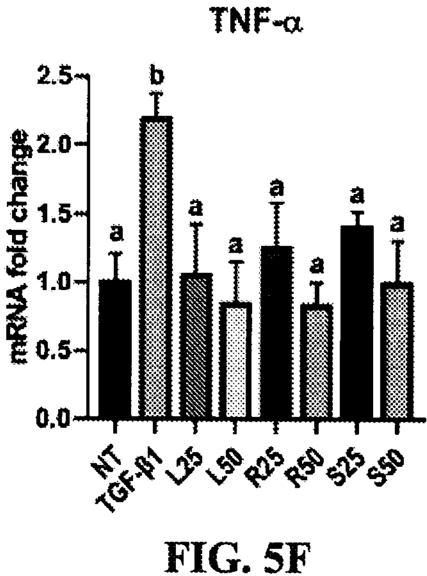
Figure 5G:
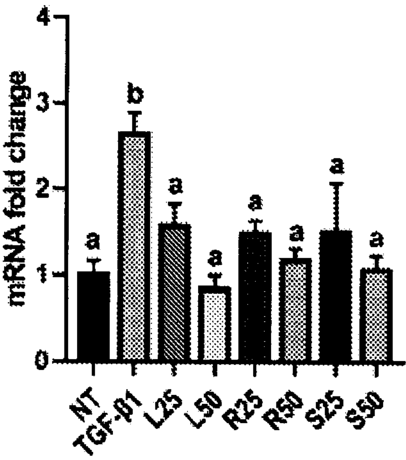
Figure 5H:
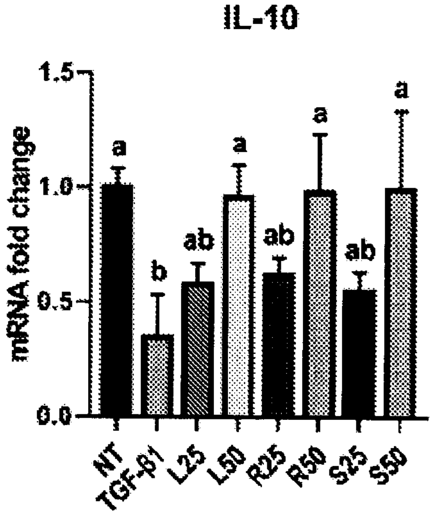

To determine the suitable doses of the *Coix lachryma-jobi* L. extract (leaf, root, and seed) for cell tests and to examine the effects of the *Coix lachryma-jobi* L. extract on cell viability (FIG. 5A). Cell viability showed that leaf and root extracts of adlay at dose below 100 μg/mL and adlay seed extract at dose below 200 μg/mL did not have any significant effect (FIG. 5B). Accordingly, 20 and 50 μg/mL of *Coix lachryma-jobi* L. extracts were used for the subsequent tests. Fibrotic marker expressions in HSC-T6 cells treated with TGF-β1 were detected using Western blot analysis. Results demonstrated that all *Coix lachryma-jobi* L. extracts dose-dependently reduced the expression of α-SMA and COL1A induced by TGF-β1 (FIGS. 5C-5E). Furthermore, for inflammation, the mRNA levels of TNF-α, IL-6, and IL-10 were assessed using real-time PCR. Results showed that all *Coix lachryma-jobi* L. extracts downregulated TGF-β1-induced TNF-α and IL-6 mRNA levels as well as upregulated the IL-10 mRNA level in a dose-dependent manner (FIGS. 5F-5H). Variations in fibrotic protein and inflammatory genes indicated that the *Coix lachryma-jobi* L. extract ameliorated inflammation and HSC activation in HSC-T6 cells treated with TGF-β1.

Example 6

Schematic Diagram of Animal Experiment Design in 6-Methoxybenzoxazolinone (6-MBOA) (CX) Groups To examine the effects of CX on liver fibrosis, this example established a TAA-induced liver fibrotic C57BL/6J mouse model. FIG. 6 is a schematic diagram of animal experiment design in 6-methoxybenzoxazolinone (6-MBOA) (CX) groups. For animal experiments, 6-week-old C57BL/6J mice were randomly divided into four groups including NT, TAA, CX20 (TAA+20 mg/kg CX), CX50 (TAA+50 mg/kg CX). (n=8 per group). Mice were given intraperitoneal injection of TAA thrice a week to induce liver fibrosis; they also received CX or the vehicle by oral gavage once per day. At the end of animal tests, mice were sacrificed at 12 weeks of age. Six-week-old mice were randomly divided into four groups, namely NT, TAA, CX20 and CX50 (FIG. 6). Among these groups, only the NT group was oral gavaged and administered with vehicle, the TAA group was oral gavaged with vehicle and administered with TAA, and the CX groups were oral gavaged with CX and administered with TAA. Oral gavage was performed once a day while intraperitoneal injection was given thrice a week; both oral gavage and intraperitoneal injection were continuously administered for six weeks. After that, the mice were sacrificed, and their liver tissues and serum were collected for subsequent analyses.

Example 7

Effects of 6-Methoxybenzoxazolinone (6-MBOA) (CX) on Liver Histopathology and Physiological Values in TAA-Induced Liver Fibrotic Mice To observe the effects of CX on liver histopathology, liver fibrotic mice were treated with CX and liver tissues were stained with H&E and Sirius red. The fibrotic marker α-SMA and TGF-β/SMAD pathway-related proteins p-SMAD2 and p-SMAD3 in the liver sections were also examined under IHC staining.

The procedure of TGF-β1 enzyme-linked immunosorbent assay (ELISA) is as follows. The level of TGF-β1 was detected in serum by using commercial mouse ELISA kits (Invitrogen, USA) and the working procedure was followed a standard sandwich ELISA protocol. Briefly, the serum was added into the TGF-β1 antibody-coated microwell, then sequentially incubated with biotin-conjugate, streptavidin-HRP, substrate solution, and stop solution. After reacted with stop solution, immediately measured the color intensity at 450 nm by ELISA reader (TECAN, Switzerland).

Figure 7B:
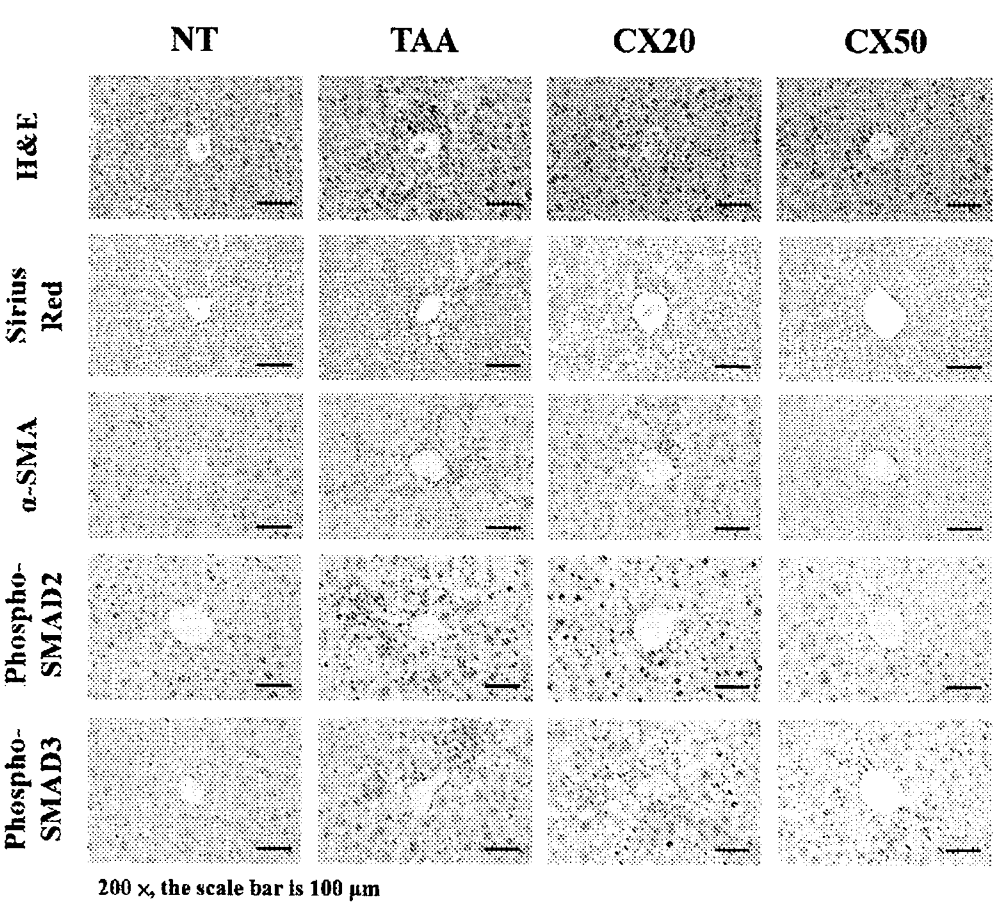
Figure 7C:
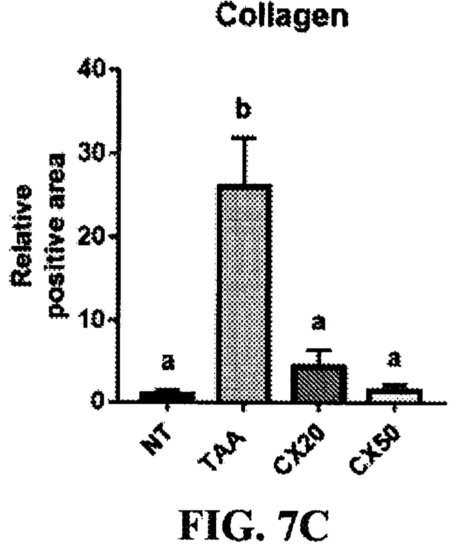
Figure 7D:
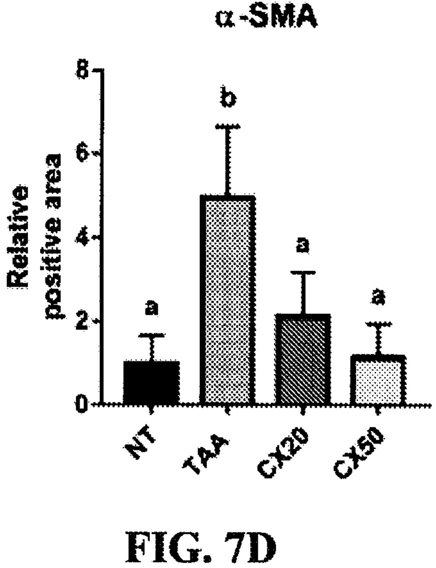
Figure 7E:
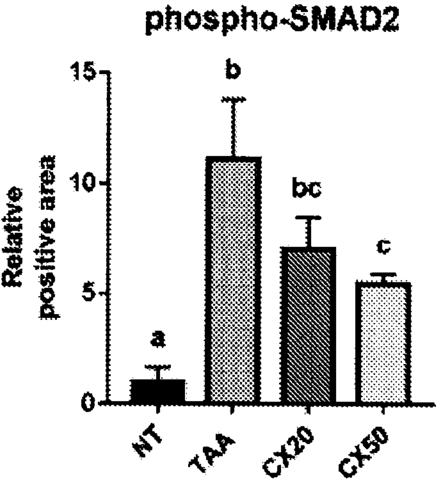
Figure 7F:
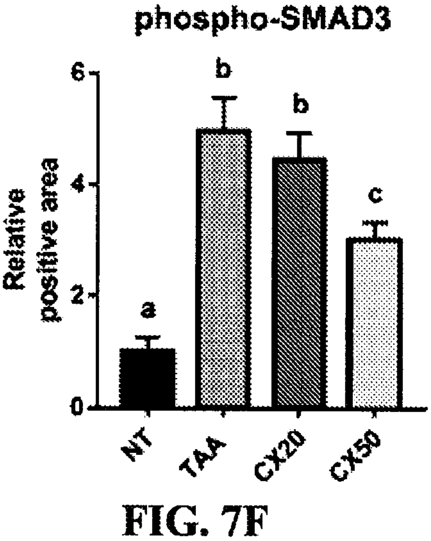
Figure 7G:
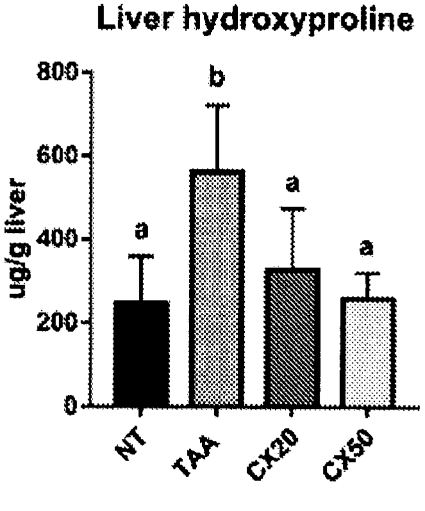
Figure 7H:
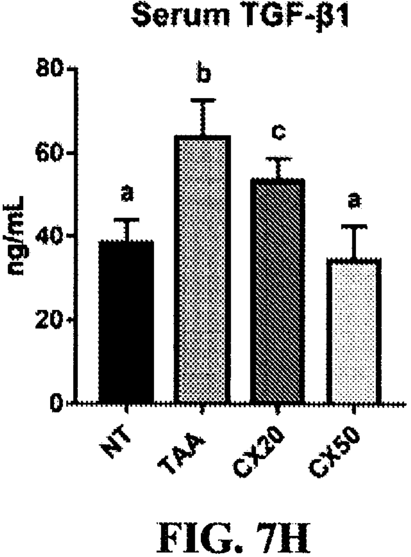
Figure 7I:
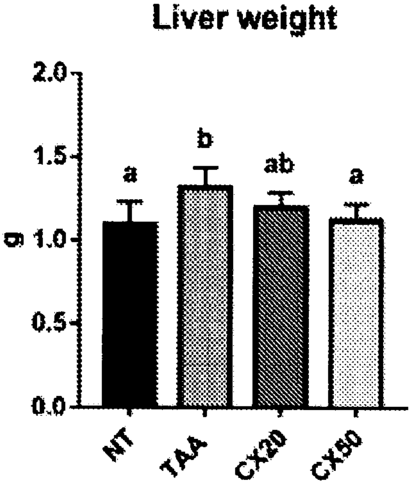
Figure 7J:
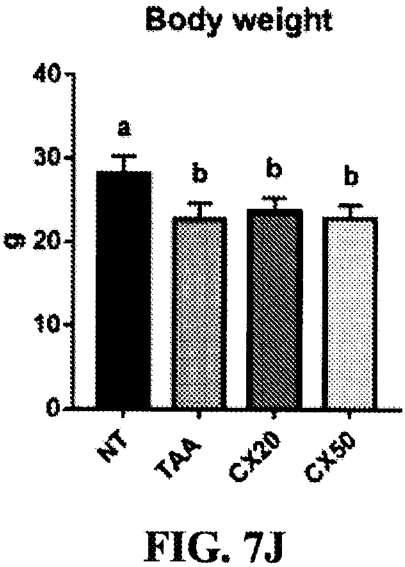
Figure 7K:
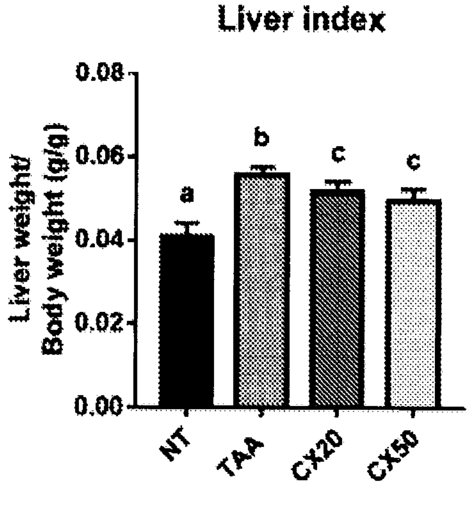
Figure 8A:
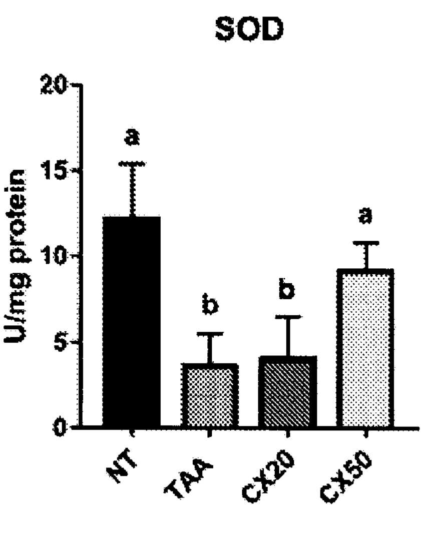
FIGS. 8A-8D show effects of CX on antioxidant enzymes and lipid peroxidation in TAA-induced liver fibrotic C57BL/6J mice. (8A, 8B) Activity changes of superoxide dismutase (SOD) and catalase (CAT). (8C) Content changes of glutathione (GSH). (8D) Content changes of malondialdehyde (MDA). Data were presented as mean±SD (n=8 per group). The bars are marked with different letters; the same letter indicates no significant difference between the two groups ($p>0.05$) while different letters indicate a significant difference between the two groups ($p<0.05$).
Figure 8B:
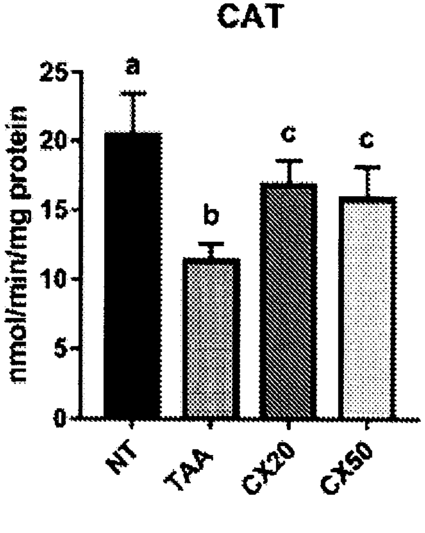
Figure 8C:
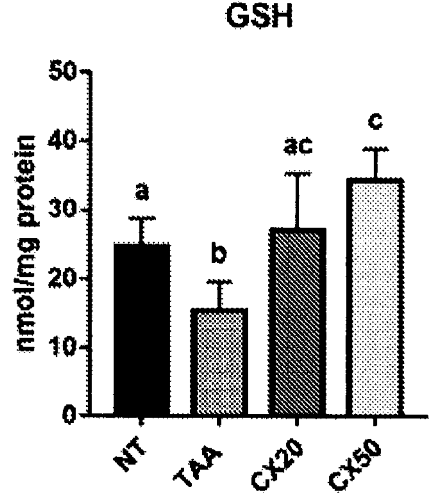
Figure 8D:
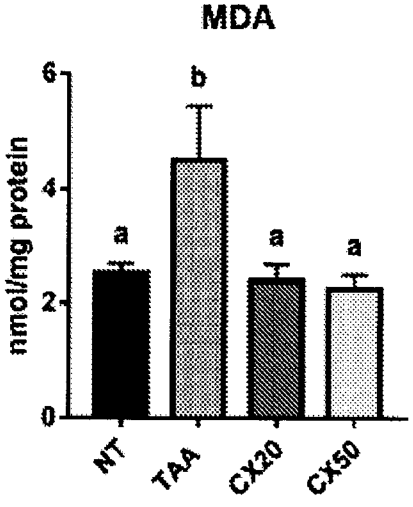

FIGS. 7A-7K show effects of CX on liver histopathology and physiological values in TAA-induced liver fibrotic C57BL/6J mice. (7A) Chemical structure of CX ($C_8H_7NO_3$, MW=165.15). (7B) Histological changes of liver observed with H&E, Sirius Red and IHC staining (original magnification×200, and the scale bar is 100 μm). (7C) Quantifications of Sirius Red staining of collagen. (7D-7F) Quantifications of IHC staining of α-SMA, phosphor-Mothers against decapentaplegic homolog 2 (phospho-SMAD2), and phosphor-Mothers against decapentaplegic homolog 3 (phospho-SMAD3). (7G) Changes in liver hydroxyproline contents. (7H) Expression of TGF-β1 in serum. (7I, 7J) Changes in liver and body weights. (7K) Liver index, ratio of liver weight to body weight. Quantifications of Sirius Red and IHC staining is achieved by using image J software. Data were presented as mean±SD (n=8 per group). The bars are marked with different letters; the same letter indicates no significant difference between the two groups ($p>0.05$) while different letters indicate a significant difference between the two groups ($p<0.05$). Compared with the NT group, the TAA group showed inflammatory infiltration, liver structure deformation, collagen deposition, and excessive expression of α-SMA and p-SMAD2/3 (FIGS. 7B-7F). Both CX20 and CX50 groups showed significantly reduced inflammatory infiltration, liver structure deformation, collagen deposition, and α-SMA expression. Furthermore, the CX50 group negatively regulated p-SMAD2 and p-SMAD3 expressions, implying that CX improved TAA-induced injury through SMAD signaling pathways. The hydroxyproline content of the TAA group was significantly higher than that of the NT group, while the CX groups had significantly lower hydroxyproline content than the TAA group, implying that CX treatment decreased collagen contents (FIG. 7G). TGF-β1 is an important cytokine associated with fibrosis, a change in TGF-β1 may be an indicator of the development of fibrosis. Results of ELISA showed that TGF-β1 expression increased significantly in the TAA group compared with the NT group, while CX significantly reduced the upregulation of TGF-β1 caused by TAA (FIG. 7H). Injection of TAA alone caused liver enlargement and body weight loss, while treatment with CX reduced liver weight, but did not significantly improve the change in body weight caused by TAA (FIGS. 7I and 7J). To avoid individual differences in mice, liver and body weights were adjusted using the liver index. Findings showed that the liver index increased significantly in the TAA group compared with the NT group, while the liver indexes in CX groups decreased significantly compared with the TAA group (FIG. 7K). The current results revealed that CX attenuated the classic characterization of fibrosis, such as excessive α-SMA expression, collagen accumulation, and higher level of TGF-β1 through affecting the expression of SMADs.

Example 8

Effects of CX on Oxidative Stress and Biochemical Characterizations in TAA-Induced Liver Fibrotic Mice Liver damages were caused by an active metabolite of TAA that leads to oxidative stress. Antioxidant enzymes superoxide dismutase (SOD), catalase (CAT), and glutathione (GSH), as well as the lipid peroxidation product malondialdehyde (MDA), were employed to detect oxidative stress in TAA-induced fibrotic mice.

The procedure of oxidative stress indicator tests is as follows. The enzyme activity of catalase (CAT) and superoxide dismutase (SOD), the content of malondialdehyde (MDA), and the concentration of glutathione (GSH) in tissue were tested to examine changes in oxidative stress levels in TAA-induced liver fibrotic mice. The hydroxyproline is the component of collagen precursor which was tested for All of the kits were commercial products, the working protocol followed the manufacturer's instructions. Briefly, the liver tissue was homogenized in ice-cold buffer and centrifuged at 4° C., then collected supernatant for analysis, finally, read the absorbance of samples with ELISA reader (TECAN, Switzerland).

FIGS. 8A-8D show effects of CX on antioxidant enzymes and lipid peroxidation in TAA-induced liver fibrotic C57BL/6J mice. (8A, 8B) Activity changes of superoxide dismutase (SOD) and catalase (CAT). (8C) Content changes of glutathione (GSH). (8D) Content changes of malondialdehyde (MDA). Data were presented as mean±SD (n=8 per group). The bars are marked with different letters; the same letter indicates no significant difference between the two groups ($p>0.05$) while different letters indicate a significant difference between the two groups ($p<0.05$). Compared with the TAA group, both CX20 and CX50 groups showed increased CAT activities and GSH contents, but decreased MDA contents. Moreover, SOD activities were significantly increased in the CX50 group.

FIGS. 9A-9G show effects of CX on liver function and nutrient metabolism in TAA-induced liver fibrotic C57BL/6J mice. (9A-9D) Serum levels of liver functional indexes ALT, AST, TBIL, and ALP. (9E-9G) Serum levels of TG, TC, and glucose for observing nutrient metabolism. Data were presented as mean±SD (n=8 per group). The bars are marked with different letters; the same letter indicates no significant difference between the two groups ($p>0.05$) while different letters indicate a significant difference between the two groups ($p<0.05$). ALP represents adlay leaf powder.

Figure 9A:
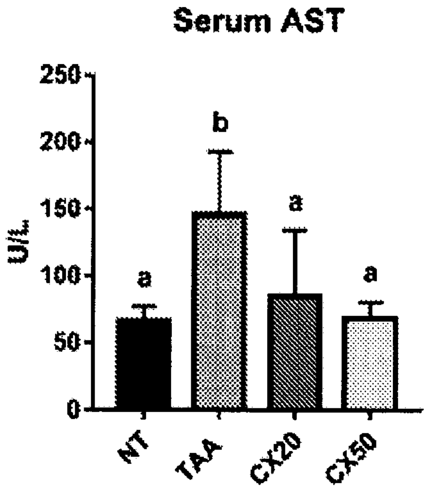
FIGS. 9A-9G show effects of CX on liver function and nutrient metabolism in TAA-induced liver fibrotic C57BL/6J mice. (9A-9D) Serum levels of liver functional indexes ALT, AST, TBIL, and alkaline phosphatase (ALP). (9E-9G) Serum levels of TG, TC, and glucose for observing nutrient metabolism. Data were presented as mean±SD (n=8 per group). The bars are marked with different letters; the same letter indicates no significant difference between the two groups ($p>0.05$) while different letters indicate a significant difference between the two groups ($p<0.05$). ALP represents adlay leaf powder.
Figure 9B:
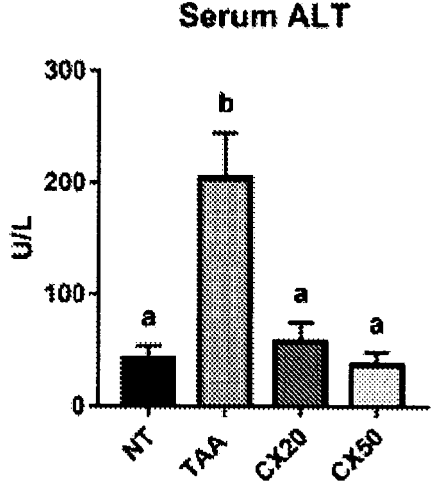
Figure 9C:
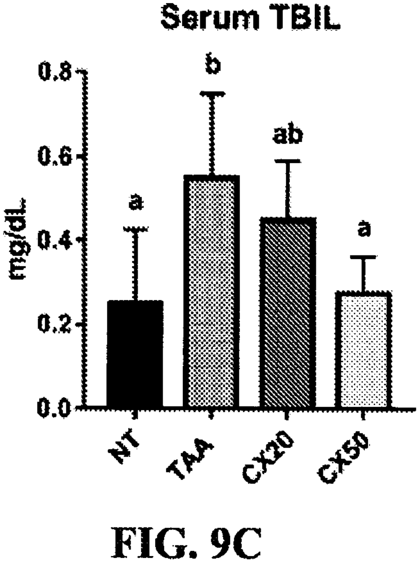
Figure 9D:
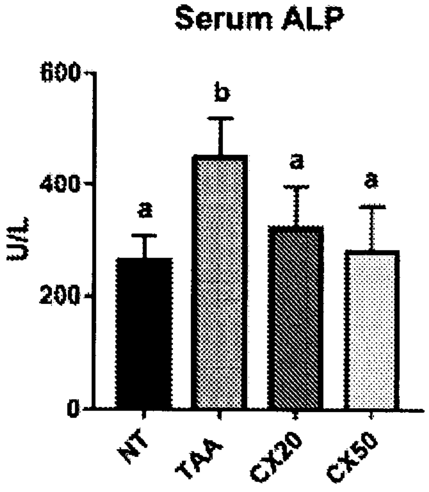
Figures 9E, 9F:
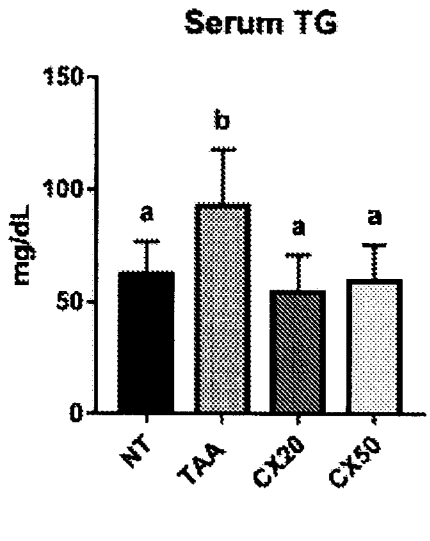
Figure 9G:
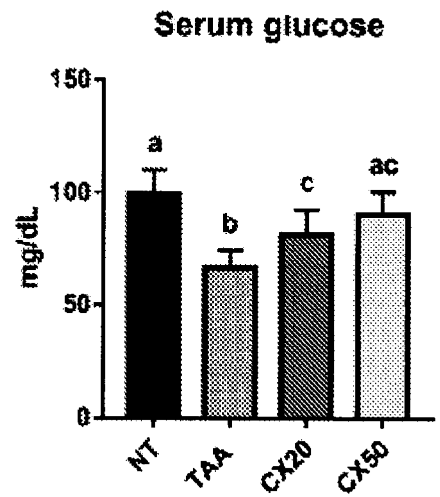

In terms of biochemical characterizations, the liver functional indices AST, ALT, TBIL, and ALP increased considerably in the TAA group compared with the NT group, but decreased significantly in the CX groups compared with the TAA group (FIGS. 9A-9D). Furthermore, TAA also caused a derangement of the nutrient metabolism. Compared with the NT group, the TAA group had significantly increased TG and TC levels but decreased glucose level, while CX significantly reduced changes in TG, TC and glucose levels caused by TAA (FIGS. 9E-9G). These findings revealed that CX relieved oxidative stress in liver and improved abnormal liver functions caused by TAA.

Example 9

Effects of CX on Fibrotic and Inflammatory Gene Levels in TAA-Induced Liver Fibrotic Mice To confirm the changes of the fibrotic gene in mice, the mRNA levels of fibrotic genes were detected using real-time PCR. FIGS. 10A-10E show effects of CX on fibrotic and inflammatory gene levels in TAA-induced liver fibrotic C57BL/6J mice. (10A, 10B) Liver mRNA levels of α-SMA and COL1A1 detected using real-time PCR. (10C-10E) Liver mRNA levels of inflammatory factors TNF-α, IL-6, and IL-10. Data were presented as mean±SD (n=8 per group). The bars are marked with different letters; the same letter indicates no significant difference between the two groups ($p>0.05$) while different letters indicate a significant difference between the two groups ($p<0.05$).

Figure 10A:
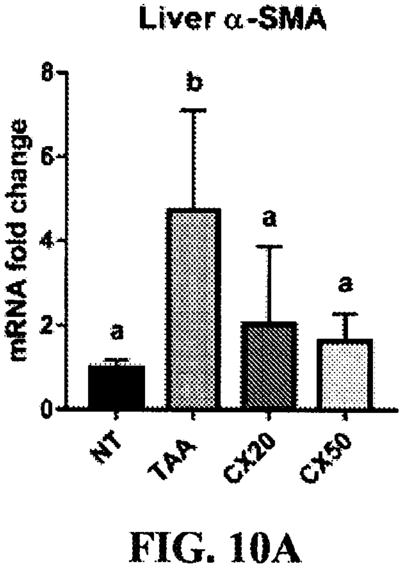
FIGS. 10A-10E show effects of CX on fibrotic and inflammatory gene levels in TAA-induced liver fibrotic C57BL/6J mice. (10A, 10B) Liver mRNA levels of α-SMA and COL1A1 detected using real-time PCR. (10C-10E) Liver mRNA levels of inflammatory factors TNF-α, IL-6, and IL-10. Data were presented as mean±SD (n=8 per group). The bars are marked with different letters; the same letter indicates no significant difference between the two groups ($p>0.05$) while different letters indicate a significant difference between the two groups ($p<0.05$).
Figure 10B:
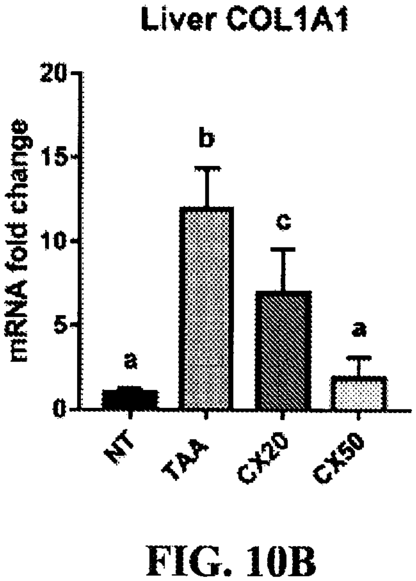
Figure 10C:
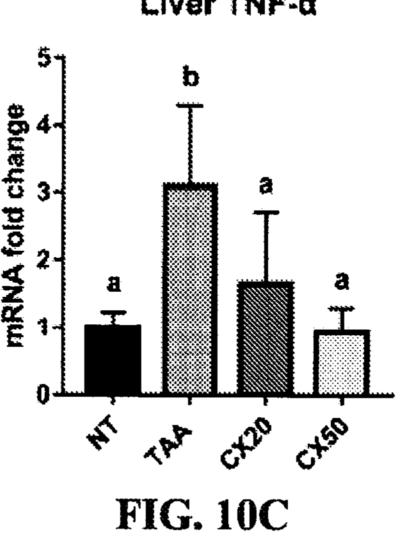
Figure 10D:
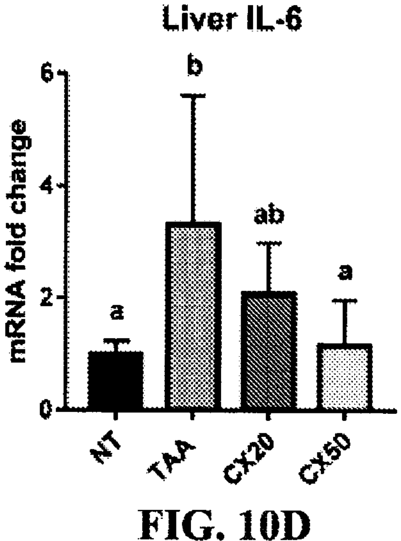
Figure 10E:
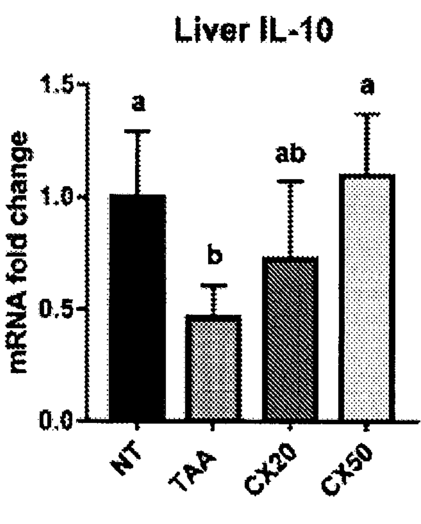

Compared with the NT group, the TAA group had significantly upregulated α-SMA and COL1A1 mRNA levels, while the CX groups had significantly decreased TAA-induced upregulation of fibrotic markers (FIGS. 10A and 10B). Inflammation is necessary for the development of fibrosis; hence, inflammatory gene mRNA levels were detected. Compared with the NT group, the TAA group showed induced upregulation of IL-6 and TNF-α, and downregulation of IL-10. CX treatment significantly decreased TAA-induced upregulation of IL-6 and TNF-α levels and downregulation of IL-10 mRNA levels (FIGS. 10C-10E). These results indicated that CX reduced inflammation and fibrogenesis at gene levels in TAA-induced fibrotic mice.

Example 10

Effects of CX on Cell Viability, Inflammatory Gene Levels, and ROS Levels in HSC-T6 Cells To examine the cell cytotoxicity of CX and determine the optimal doses for subsequent cell experiments, various doses of CX were tested in HSC-T6 cells using the MTT assay.

The procedure of ROS detection assay is as follows. 2',7'-Dichlorofluorescein diacetate (DCFDA), a cell-permeable fluorogenic probe, is usually used to detect ROS and nitric oxide in live cells. DCFDA rapidly de-esterifies to form fluorescent 2',7'-dichlorofluorescein (DCF) when it is oxidized by ROS in cells. For ROS detection, cells were seeded in the 96-well plate for 24 h, then starvation (culture in serum-free medium) and drug treatment, followed by changing the medium with DCFDA solution for 30 min, and detecting the excitation/emission spectra of 485/525 nm by multimode microplate readers (TECAN, Switzerland).

FIGS. 11A-11F show effects of CX on cell viability, inflammatory gene levels, and reactive oxygen species (ROS) in TGF-β1-activated HSC-T6 cells. (11A) Schematic representation for TGF-β1 and CX treatment in HSC-T6 cells. 6-MBOA represents 6-methoxybenzoxazolinone. (11B) Cell viability of HSC-T6 cells treated with various concentrations of CX. (11C-11E) mRNA levels of inflammatory factors in HSC-T6 cells treated with TGF-β1 and CX. (11F) ROS levels of HSC-T6 detected with DCFDA and normalized with protein contents. Data were presented as mean±SD (n=3 per group). The bars of cell viability are marked with *, 0 of concentration vs. other concentrations, marked with *** (P<0.001). The bars of western blot and real-time PCR are marked with different letters; the same letter indicates no significant difference between the two samples (p>0.05) while different letters indicate a significant difference between the two group (p<0.05).

Figure 11A:
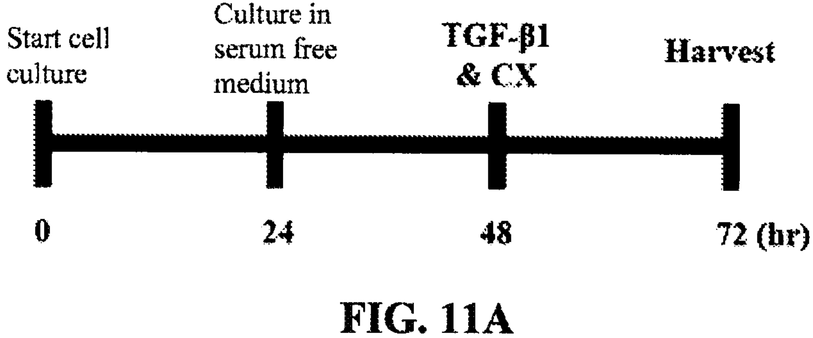
FIGS. 11A-11F show effects of CX on cell viability, inflammatory gene levels, and reactive oxygen species (ROS) in TGF-β1-activated HSC-T6 cells. (11A) Schematic representation for TGF-β1 and CX treatment in HSC-T6 cells. 6-MBOA represents 6-methoxybenzoxazolinone. (11B) Cell viability of HSC-T6 cells treated with various concentrations of CX. (11C-11E) mRNA levels of inflammatory factors in HSC-T6 cells treated with TGF-β1 and CX. (11F) ROS levels of HSC-T6 detected with DCFDA and normalized with protein contents. Data were presented as mean±SD (n=3 per group). The bars of cell viability are marked with *, 0 of concentration vs. other concentrations, marked with *** ($P<0.001$). The bars of western blot and real-time PCR are marked with different letters; the same letter indicates no significant difference between the two samples ($p>0.05$) while different letters indicate a significant difference between the two group ($p<0.05$).
Figure 11B:
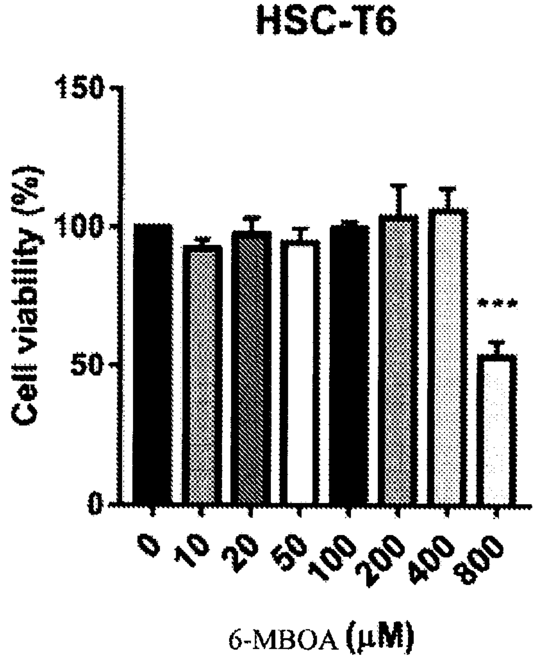
Figure 11C:
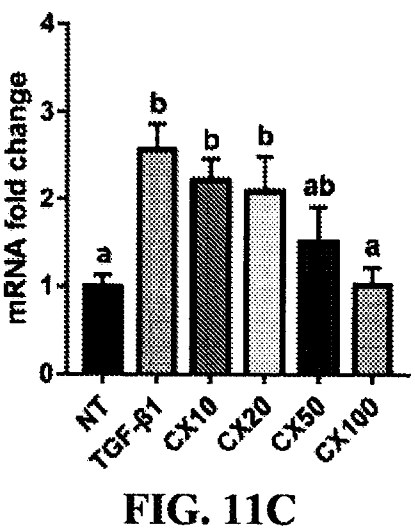
Figure 11D:
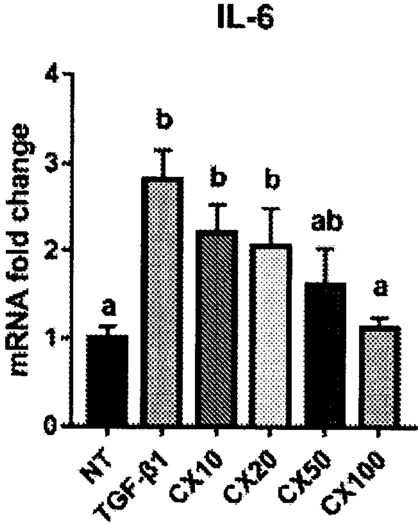
Figure 11E:
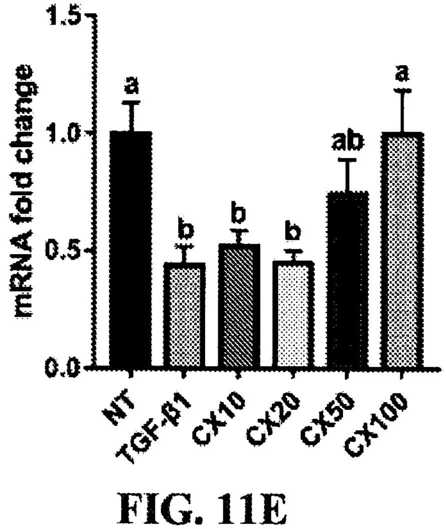
Figure 11F:
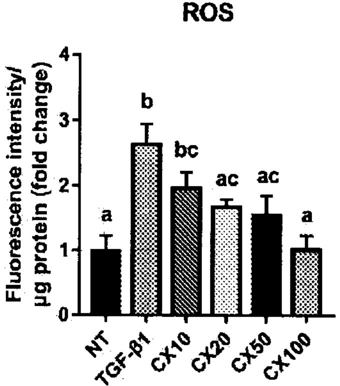

Results showed no significant effects at a dose below 400 μM; hence, 10, 20, 50, and 100 μM were used for subsequent cell assays (FIG. 11B). Similarly, the mRNA levels of TNF-α, IL-6, and IL-10 in HSC-T6 cells treated with TGF-β1 were detected using real-time PCR. Results showed that TGF-β1 treatment significantly increased TNF-α, and IL-6, and decreased IL-10 mRNA levels (FIGS. 11C-E), while CX dose-dependently decreased TGF-β1-induced TNF-α, and IL-6, and significantly increased IL-10 mRNA levels at the highest dose. Furthermore, ROS levels in HSC-T6 cells were detected using the DCFDA assay. Findings showed that TGF-β1 induced ROS production, while CX reduced TGF-β1-induced ROS levels with increasing doses (FIG. 11F). These results revealed that TGF-β1 promoted inflammation and the production of ROS, while CX exhibited the potential to reduce inflammation and ROS in HSC-T6 cells activated with TGF-β1.

Example 11

Effects of CX on HSC Activation and Epithelial-Mesenchymal Transition (EMT) in HSC-T6 Cells To understand the effects of CX on HSC activation and EMT in TGF-β1-activated HSC-T6 cells, the expressions of fibrotic and EMT-related proteins were examined using Western blot analysis.

The procedure of wound healing assay is as follows. HSC-T6 cells were seeded on the 6-well plates for 24 h, scraped monolayer cells with a 200 μL pipette tip and washed off non-adherent cells by PBS, changed serum-free medium for 24 h, then treated with TGF-β1 and CX for 0, 24, and 48 h. The images of cell migration were observed with inverted microscopy (Olympus, Japan), and the wound areas were quantified by image J software.

FIGS. 12A-12G show effects of CX on HSC activation and epithelial-mesenchymal transition (EMT) in TGF-β1-activated HSC-T6 cells. (12A) Western blot results of E-cadherin, fibronectin, α-SMA, and COL1A1 (12B-12E) Quantifications of Western blots of E-cadherin, fibronectin, α-SMA, and COL1A1 using image J software. (12F, 12G) Results of wound healing assay at 0, 24, and 48 hours (magnification×200, the scale bar is 100 μm), and quantified using image J software. Wound closure is defined as (wound area of 0 h−wound area of 24 or 48 h)/wound area of 0 h×100%. Data were presented as mean±SD (n=3 per group). The bars of data are marked with different letters; the same letter indicates no significant difference between the two groups (p>0.05) while different letters indicate a significant difference between the two groups (p<0.05).

Figure 12A:
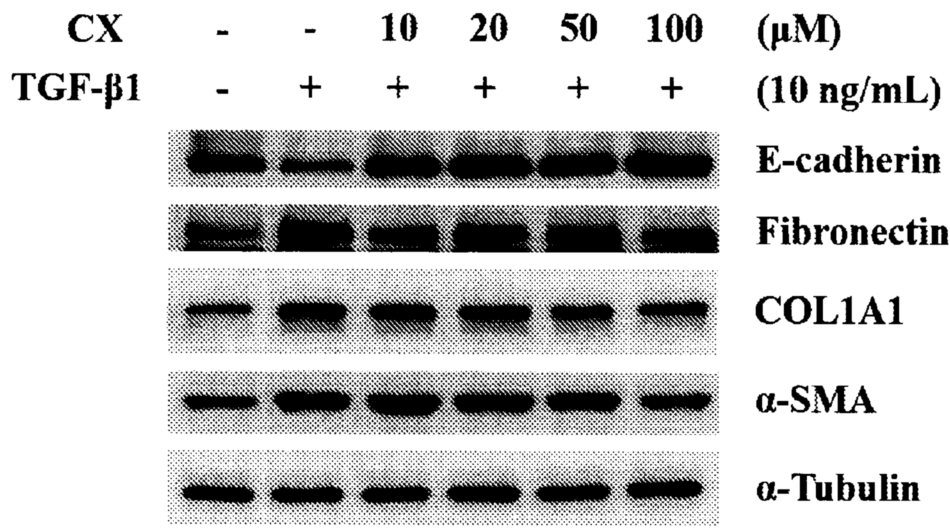
FIGS. 12A-12G show effects of CX on HSC activation and epithelial-mesenchymal transition (EMT) in TGF-β1-activated HSC-T6 cells. (12A) Western blot results of E-cadherin, fibronectin, α-SMA, and COL1A1 (12B-12E) Quantifications of Western blots of E-cadherin, fibronectin, α-SMA, and COL1A1 using image J software. (12F, 12G) Results of wound healing assay at 0, 24, and 48 hours (magnification×200, the scale bar is 100 μm), and quantified using image J software. Wound closure is defined as (wound area of 0 h−wound area of 24 or 48 h)/wound area of 0 h×100%. Data were presented as mean±SD (n=3 per group). The bars of data are marked with different letters; the same letter indicates no significant difference between the two groups ($p>0.05$) while different letters indicate a significant difference between the two groups ($p<0.05$).
Figure 12B:
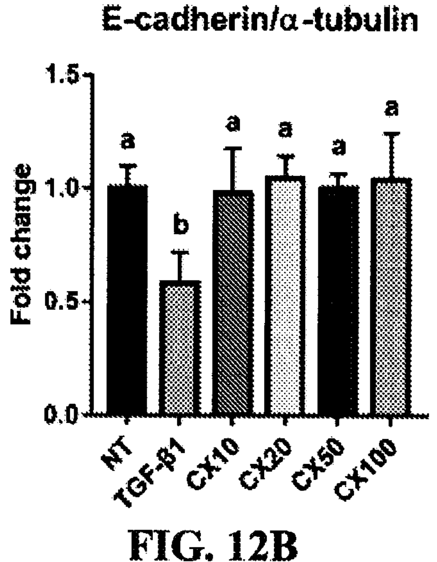
Figure 12C:
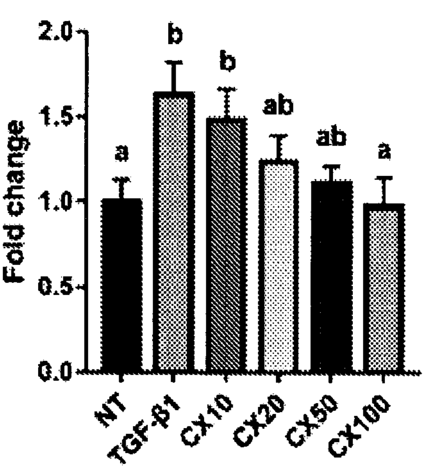
Figure 12D:
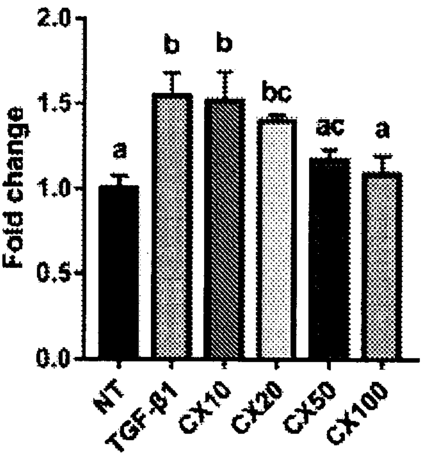
Figure 12E:
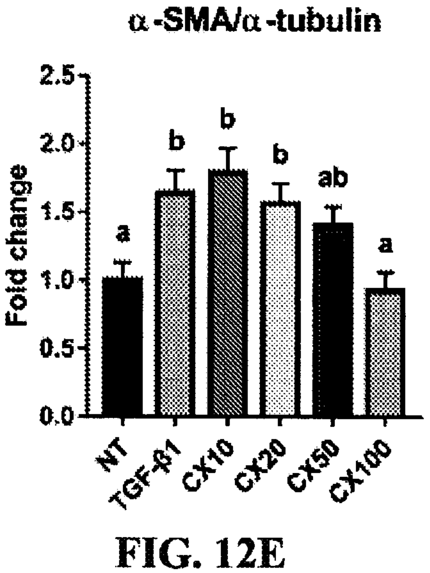
Figure 12F:
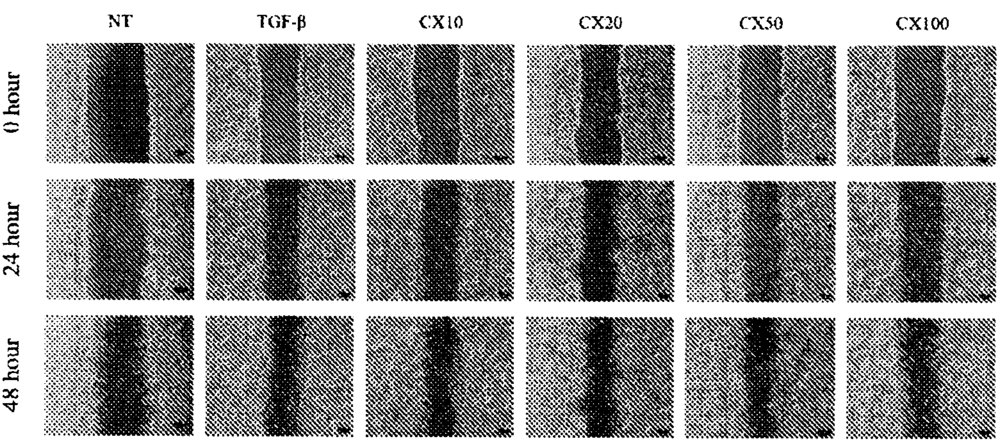
Figure 12G:
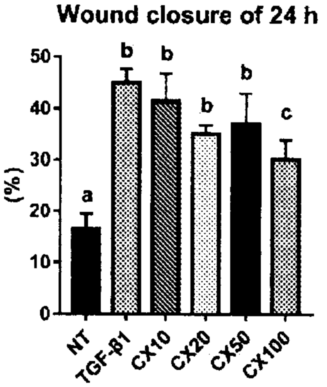
Figure 12G:
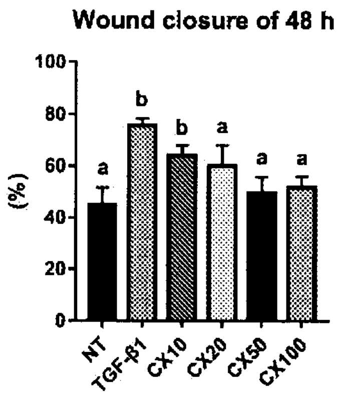
Figures 13A, 13B:
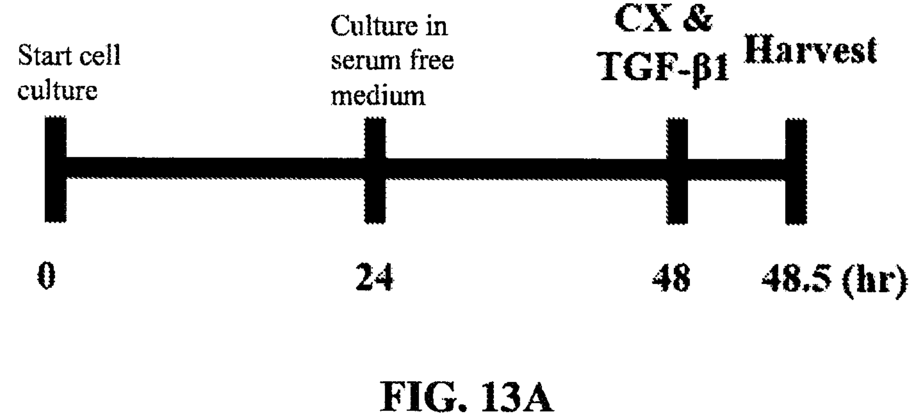
FIGS. 13A-13I show effects of CX on TGF-β/SMAD signaling pathway in TGF-β1-activated HSC-T6 cells. (13A) Schematic representation for stimulation of TGF-β1 pathway and CX treatment in HSC-T6 cells. (13B) Western blot results of phosphor-Mothers against decapentaplegic homolog 2 (p-SMAD2), phosphor-Mothers against decapentaplegic homolog 3 (p-SMAD3), SMAD2/3, Zinc finger protein SNAIL1/2, TWIST1/2, Zinc finger E-box-binding homeobox 1 (ZEB1), and NADPH oxidase 4 (NOX4) normalized with α-tubulin. (13C-13I) Quantifications of Western blots of p-SMAD2, p-SMAD3, SMAD2/3, SNAIL1/2, TWIST1/2, ZEB1, and NOX4 using image J software. Data were presented as mean±SD (n=3 per group). The bars of data are marked with different letters; the same letter indicates no significant difference between the two samples ($p>0.05$) while different letters indicate a significant difference between the two groups ($p<0.05$).
Figure 13C:
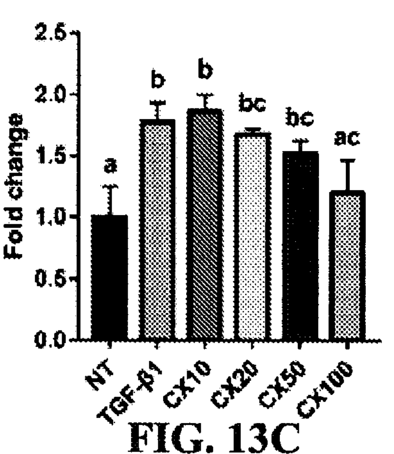
Figure 13D:
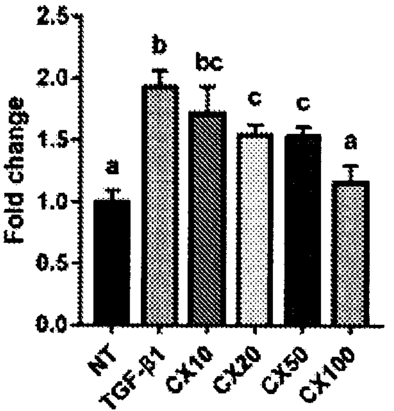
Figure 13E:
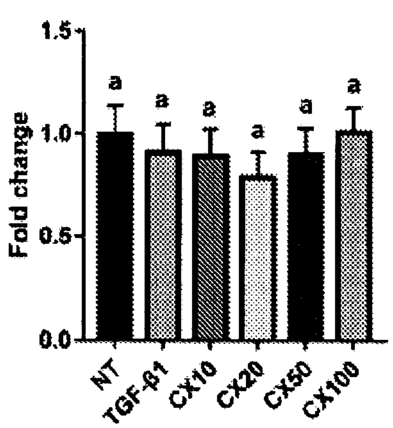
Figure 13F:
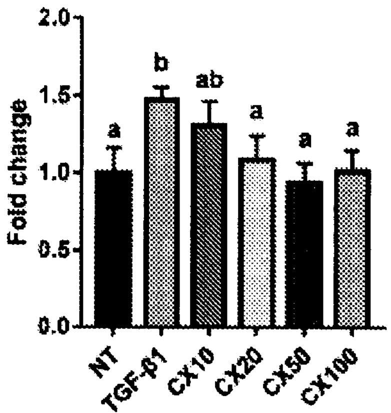
Figure 13G:
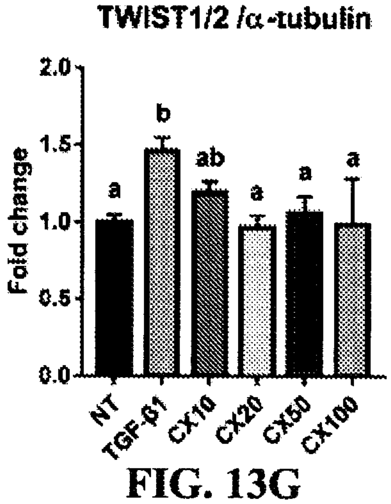
Figure 13H:
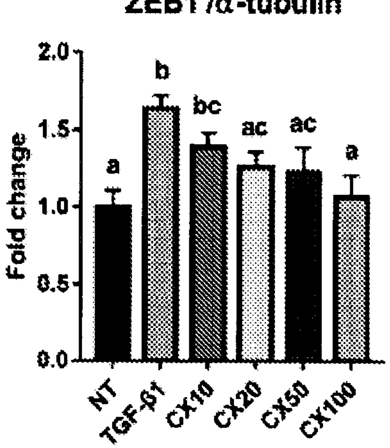
Figure 13I:
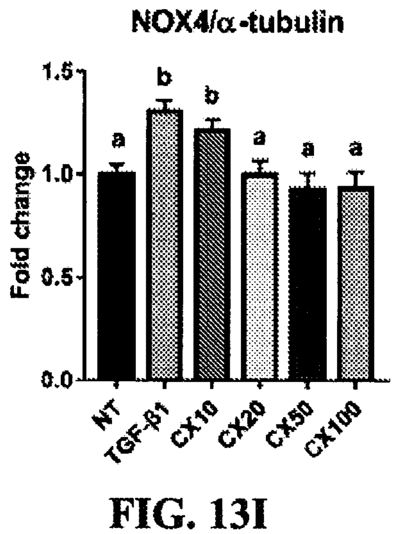

TGF-β1 treatment upregulated the expressions of α-SMA, COL1A1, and the mesenchymal marker fibronectin, as well as downregulated epithelial marker E-cadherin (FIGS. 12A-12E). Treatment with CX reduced TGF-β1-induced α-SMA, COL1A1 and fibronectin expressions but significantly enhanced E-cadherin expression even at the lowest dose. As EMT occurs, cell migration ability may be enhanced. Hence, migration changes were examined using a wound healing assay. The percentage of wound closure increased significantly in the TGF-β1 group compared with the NT group (FIGS. 12F and 12G). TGF-β1-induced wound closure of 24 h was significantly reduced by CX treatment at a dose of 100 μM, while TGF-β1-induced wound closure of 48 h was reduced by CX treatment at a dose of 20-100 μM. These results suggested that CX inhibited HSC activation and EMT in HSC-T6 cells treated with TGF-β1.

Example 12

Effects of CX on TGF-β/Mothers Against Decapentaplegic Homolog (SMAD) Pathway in HSC-T6 Cells The mechanisms of CX on HSC activation and EMT were further explored using Western blot analysis.

FIGS. 13A-13I show effects of CX on TGF-β/SMAD signaling pathway in TGF-β1-activated HSC-T6 cells. (13A) Schematic representation for stimulation of TGF-β1 pathway and CX treatment in HSC-T6 cells. (13B) Western blot results of phosphor-Mothers against decapentaplegic homolog 2 (p-SMAD2), phosphor-Mothers against decapentaplegic homolog 3 (p-SMAD3), SMAD2/3, Zinc finger protein SNAIL1/2, TWIST1/2, Zinc finger E-box-binding homeobox 1 (ZEB1), and NADPH oxidase 4 (NOX4) normalized with α-tubulin. (13C-13I) Quantifications of Western blots of p-SMAD2, p-SMAD3, SMAD2/3, SNAIL1/2, TWIST1/2, ZEB1, and NOX4 using image J software. Data were presented as mean±SD (n=3 per group). The bars of data are marked with different letters; the same letter indicates no significant difference between the two samples (p>0.05) while different letters indicate a significant difference between the two groups (p<0.05).

The expressions of SMAD pathway-related proteins phospho-SMAD2, phospho-SMAD3, EMT-related proteins SNAIL1/2, TWIST1/2, ZEB1 and ROS-related protein NOX4 increased significantly in the TGF-β1 group compared with the NT group (FIGS. 13B-13I), indicating that TGF-β1 could phosphorylate SMAD2 and SMAD3, then activate downstream proteins SNAIL1/2, TWIST1/2, ZEB1 and NOX4, further causing ROS production and triggering EMT. When treated with CX, TGF-β1-stimulated SMAD phosphorylation and downstream protein expression decreased with increasing dose, revealing that CX decreased the expression of SNAIL1/2, TWIST1/2, and ZEB1 and NOX4, and further prevented EMT and ROS production by inhibiting SMAD2 and SMAD3 phosphorylation.

Figure 14A:
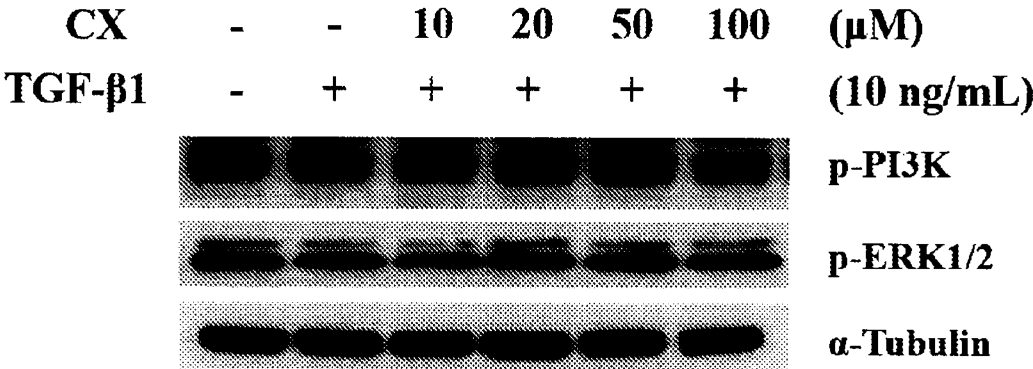
FIGS. 14A-14C show effects of CX on phosphoinositide 3-kinase (PI3K) and extracellular signal-regulated kinase (ERK) signaling pathway in TGF-β1-activated HSC-T6 cells. (14A) Western blot results of p-PI3K and p-ERK1/2 normalized with α-tubulin. (14B, 14C) Western blot quantifications of p-PI3K and p-ERK1/2 using image J. Data were presented as mean±SD (n=3 per sample). The bars of data are marked with different letters; the same letter indicates no significant difference between the two groups ($p>0.05$) while different letters indicate a significant difference between the two groups ($p<0.05$).
Figure 14B:
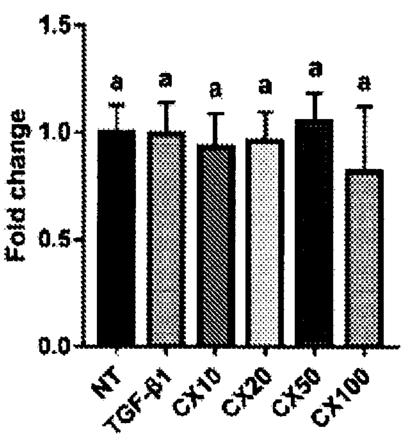
Figure 14C:
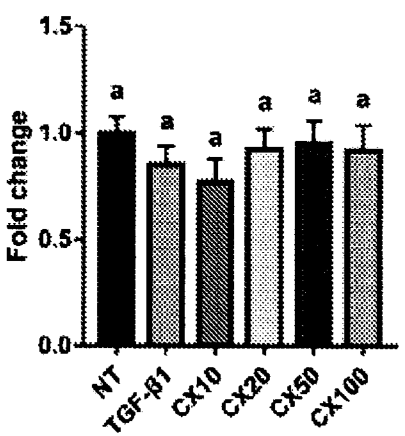

FIGS. 14A-14C show effects of CX on phosphoinositide 3-kinase (PI3K) and extracellular signal-regulated kinase (ERK) signaling pathway in TGF-β1-activated HSC-T6 cells. (14A) Western blot results of p-PI3K and p-ERK1/2 normalized with α-tubulin. (14B, 14C) Western blot quantifications of p-PI3K and p-ERK1/2 using image J. Data were presented as mean±SD (n=3 per sample). The bars of data are marked with different letters; the same letter indicates no significant difference between the two groups ($p>0.05$) while different letters indicate a significant difference between the two groups ($p<0.05$).

As for the non-SMAD pathway, results showed that CX did not cause significant changes in phosphorylation of PI3K and ERK, suggesting that CX has little effect on the ERK and PI3K signaling pathways (FIGS. 14A-14C).

In summary, 6-MBOA (CX) and the *Coix lachryma-jobi* L. extract comprising 6-MBOA of the present invention achieve the effect on preventing liver fibrosis in vivo and in vitro, accompanied with downregulation of fibrotic and inflammatory factors. Furthermore, 6-MBOA ameliorates oxidative stress in liver, as well as reduces the production of liver fibrotic biomarkers and promotes the loss of mesenchymal identity of HSC through the TGF-β/SMAD signaling pathway. Both 6-MBOA and the *Coix lachryma-jobi* L. extract comprising 6-MBOA possess therapeutic potential for liver fibrosis.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A method for treating liver fibrosis in a subject, wherein the method comprises administering to the subject in need thereof a pharmaceutical composition comprising a pharmaceutically acceptable excipient, carrier, or adjuvant, or a combination thereof, and a therapeutically effective amount of 6-methoxybenzoxazolinone (6-MBOA) of the following structural formula:

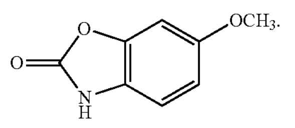 [SMILES: COc1ccc2[nH]c(=O)oc2c1]

2. The method according to claim 1, wherein the pharmaceutical composition is a comestible composition or a topical composition.

3. The method according to claim 2, wherein the comestible composition further comprises a food additive.

4. The method according to claim 1, wherein the pharmaceutical composition is formulated for oral administration.

5. The method according to claim 1, wherein the pharmaceutical composition is formulated for parenteral administration.

6. The method according to claim 1, wherein the pharmaceutical composition is formulated as a granule, a jelly, a paste, a powder, or a solution.

7. A method for treating liver fibrosis in a subject, wherein the method comprises administering to the subject in need thereof a pharmaceutical composition comprising a pharmaceutically acceptable excipient, carrier, or adjuvant, or a combination thereof, and a therapeutically effective amount of *Coix lachrymal-jobi* L. extract comprising 6-methoxybenzoxazolinone (6-MBOA) of the following structural formula:

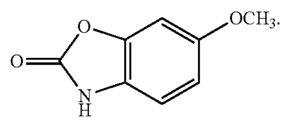 [SMILES: COc1ccc2[nH]c(=O)oc2c1]

8. The method according to claim 7, wherein the pharmaceutical composition is a comestible composition or a topical composition.

9. The method according to claim 8, wherein the comestible composition further comprises a food additive.

10. The method according to claim 7, wherein the pharmaceutical composition is formulated for oral administration.

11. The method according to claim 7, wherein the pharmaceutical composition is formulated for parenteral administration.

* * * * *

```
                    SEQUENCE LISTING

Sequence total quantity: 24
SEQ ID NO: 1            moltype = DNA  length = 20
FEATURE                 Location/Qualifiers
source                  1..20
                        mol_type = other DNA
                        organism = synthetic construct
SEQUENCE: 1
gctctggtgt gtgacaatgg                                              20

SEQ ID NO: 2            moltype = DNA  length = 20
FEATURE                 Location/Qualifiers
source                  1..20
                        mol_type = other DNA
                        organism = synthetic construct
SEQUENCE: 2
cttttccatg tcgtcccagt                                              20

SEQ ID NO: 3            moltype = DNA  length = 20
FEATURE                 Location/Qualifiers
source                  1..20
                        mol_type = other DNA
                        organism = synthetic construct
SEQUENCE: 3
tgttcagctt tgtggacctc                                              20

SEQ ID NO: 4            moltype = DNA  length = 20
FEATURE                 Location/Qualifiers
source                  1..20
                        mol_type = other DNA
                        organism = synthetic construct
SEQUENCE: 4
gccattgtgg cagatacaga                                              20

SEQ ID NO: 5            moltype = DNA  length = 22
FEATURE                 Location/Qualifiers
source                  1..22
                        mol_type = other DNA
                        organism = synthetic construct
SEQUENCE: 5
ggcacagtca aggctgagaa tg                                           22

SEQ ID NO: 6            moltype = DNA  length = 21
FEATURE                 Location/Qualifiers
source                  1..21
                        mol_type = other DNA
                        organism = synthetic construct
SEQUENCE: 6
atggtggtga agacgccagt a                                            21
```

-continued

```
SEQ ID NO: 7            moltype = DNA  length = 24
FEATURE                 Location/Qualifiers
source                  1..24
                        mol_type = other DNA
                        organism = synthetic construct
SEQUENCE: 7
attgtatgaa cagcgatgat gcac                                              24

SEQ ID NO: 8            moltype = DNA  length = 23
FEATURE                 Location/Qualifiers
source                  1..23
                        mol_type = other DNA
                        organism = synthetic construct
SEQUENCE: 8
ccaggtagaa acggaactcc aga                                               23

SEQ ID NO: 9            moltype = DNA  length = 20
FEATURE                 Location/Qualifiers
source                  1..20
                        mol_type = other DNA
                        organism = synthetic construct
SEQUENCE: 9
gcgacgctgt catcgatttc                                                   20

SEQ ID NO: 10           moltype = DNA  length = 20
FEATURE                 Location/Qualifiers
source                  1..20
                        mol_type = other DNA
                        organism = synthetic construct
SEQUENCE: 10
gtagatgccg ggtggttcaa                                                   20

SEQ ID NO: 11           moltype = DNA  length = 19
FEATURE                 Location/Qualifiers
source                  1..19
                        mol_type = other DNA
                        organism = synthetic construct
SEQUENCE: 11
tcagttccat ggcccagac                                                    19

SEQ ID NO: 12           moltype = DNA  length = 24
FEATURE                 Location/Qualifiers
source                  1..24
                        mol_type = other DNA
                        organism = synthetic construct
SEQUENCE: 12
gttgtctttg agatccatgc catt                                              24

SEQ ID NO: 13           moltype = DNA  length = 21
FEATURE                 Location/Qualifiers
source                  1..21
                        mol_type = other DNA
                        organism = synthetic construct
SEQUENCE: 13
gtcccagaca tcagggagta a                                                 21

SEQ ID NO: 14           moltype = DNA  length = 21
FEATURE                 Location/Qualifiers
source                  1..21
                        mol_type = other DNA
                        organism = synthetic construct
SEQUENCE: 14
tcggatactt cagcgtcagg a                                                 21

SEQ ID NO: 15           moltype = DNA  length = 20
FEATURE                 Location/Qualifiers
source                  1..20
                        mol_type = other DNA
                        organism = synthetic construct
SEQUENCE: 15
tggattcccg ttcgagtacg                                                   20

SEQ ID NO: 16           moltype = DNA  length = 20
FEATURE                 Location/Qualifiers
source                  1..20
                        mol_type = other DNA
                        organism = synthetic construct
SEQUENCE: 16
```

-continued

```
attaggcgca ggaaggtcag                                                20

SEQ ID NO: 17           moltype = DNA  length = 20
FEATURE                 Location/Qualifiers
source                  1..20
                        mol_type = other DNA
                        organism = synthetic construct
SEQUENCE: 17
aactttggca ttgtggaagg                                                20

SEQ ID NO: 18           moltype = DNA  length = 20
FEATURE                 Location/Qualifiers
source                  1..20
                        mol_type = other DNA
                        organism = synthetic construct
SEQUENCE: 18
ggatgcaggg atgatgttct                                                20

SEQ ID NO: 19           moltype = DNA  length = 20
FEATURE                 Location/Qualifiers
source                  1..20
                        mol_type = other DNA
                        organism = synthetic construct
SEQUENCE: 19
ccagttgcct tcttgggact                                                20

SEQ ID NO: 20           moltype = DNA  length = 21
FEATURE                 Location/Qualifiers
source                  1..21
                        mol_type = other DNA
                        organism = synthetic construct
SEQUENCE: 20
ggtctgttgg gagtggtatc c                                              21

SEQ ID NO: 21           moltype = DNA  length = 21
FEATURE                 Location/Qualifiers
source                  1..21
                        mol_type = other DNA
                        organism = synthetic construct
SEQUENCE: 21
gctcttactg actggcatga g                                              21

SEQ ID NO: 22           moltype = DNA  length = 20
FEATURE                 Location/Qualifiers
source                  1..20
                        mol_type = other DNA
                        organism = synthetic construct
SEQUENCE: 22
cgcagctcta ggagcatgtg                                                20

SEQ ID NO: 23           moltype = DNA  length = 23
FEATURE                 Location/Qualifiers
source                  1..23
                        mol_type = other DNA
                        organism = synthetic construct
SEQUENCE: 23
tgggagtaga caaggtacaa ccc                                            23

SEQ ID NO: 24           moltype = DNA  length = 25
FEATURE                 Location/Qualifiers
source                  1..25
                        mol_type = other DNA
                        organism = synthetic construct
SEQUENCE: 24
catcttctca aaattcgagt gacaa                                          25
```